US010190089B2

(12) United States Patent
Bolea et al.

(10) Patent No.: US 10,190,089 B2
(45) Date of Patent: Jan. 29, 2019

(54) MODULAR SYSTEM AND METHOD FOR DETECTING MICROORGANISMS

(71) Applicant: 3M INNOVATIVE PROPERTIES COMPANY, St. Paul, MN (US)

(72) Inventors: Phillip A. Bolea, Grant, MN (US); Jon A. Kirschhoffer, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/827,574

(22) Filed: Nov. 30, 2017

(65) Prior Publication Data

US 2018/0080001 A1    Mar. 22, 2018

Related U.S. Application Data

(62) Division of application No. 12/668,092, filed as application No. PCT/US2008/069485 on Jul. 9, 2008, now Pat. No. 9,834,748.

(Continued)

(51) Int. Cl.
| | |
|---|---|
| *C12Q 1/04* | (2006.01) |
| *C12M 1/00* | (2006.01) |
| *C12M 1/34* | (2006.01) |
| *C12M 3/00* | (2006.01) |
| *C12M 1/36* | (2006.01) |

(52) U.S. Cl.
CPC .......... *C12M 41/46* (2013.01); *C12M 23/44* (2013.01); *C12M 41/48* (2013.01); *C12Q 1/04* (2013.01)

(58) Field of Classification Search
CPC ...... C12M 23/44; C12M 41/48; C12M 41/46; C12Q 1/04
See application file for complete search history.

(56) References Cited

U.S. PATENT DOCUMENTS

| | | |
|---|---|---|
| 822,354 A | 6/1906 | Duncan |
| 1,768,715 A | 7/1930 | Hopp et al. |

(Continued)

FOREIGN PATENT DOCUMENTS

| | | |
|---|---|---|
| DE | 24 43 410 C3 | 10/1981 |
| DE | 39 16 804 | 11/1989 |

(Continued)

OTHER PUBLICATIONS

Brochure entitled "MEDIAJET vario—The most versatile Petri dish filler available" from INTEGRA Biosciences AG (2 pgs.).

(Continued)

*Primary Examiner* — William H. Beisner
*Assistant Examiner* — Danielle B Henkel
(74) *Attorney, Agent, or Firm* — Eric E. Silverman

(57) ABSTRACT

A modular automated system for sample processing and/or detection of microorganisms is provided. The modular system includes modules that perform at least one function in the process of detecting microorganisms in a culture device, such as collection of multiple samples, sample loading, sample preparation, sample incubation, and detection of microorganisms in samples. An exemplary embodiment of a modular sample processing and/or detection system can include an automated loading module, a liquid processing module, modular incubator, a second automated loading module, a reader module, and a collector.

8 Claims, 15 Drawing Sheets

Related U.S. Application Data

(60) Provisional application No. 61/018,669, filed on Jan. 2, 2008, provisional application No. 60/948,687, filed on Jul. 9, 2007.

(56) References Cited

U.S. PATENT DOCUMENTS

| | | | |
|---|---|---|---|
| 3,493,772 | A | 2/1970 | Daughters, II et al. |
| 3,736,432 | A | 5/1973 | Sweet |
| 3,764,480 | A | 10/1973 | Jedlicka et al. |
| 3,811,036 | A | 5/1974 | Perry |
| 3,972,778 | A | 8/1976 | Cunningham |
| 4,116,775 | A | 9/1978 | Charles et al. |
| 4,118,280 | A | 10/1978 | Charles et al. |
| 4,456,380 | A | 6/1984 | Kondo et al. |
| 4,535,239 | A | 8/1985 | Brighton |
| 4,554,867 | A | 11/1985 | Thumm |
| 4,565,783 | A | 1/1986 | Hansen et al. |
| 4,637,053 | A | 1/1987 | Schalkowsky |
| 4,720,463 | A | 1/1988 | Farber et al. |
| 4,806,316 | A | 2/1989 | Johnson et al. |
| 4,896,966 | A | 1/1990 | Boisseau et al. |
| 5,117,467 | A | 5/1992 | Misaki et al. |
| 5,149,654 | A | 9/1992 | Gross et al. |
| 5,403,722 | A | 4/1995 | Floeder et al. |
| 5,510,246 | A | 4/1996 | Morgan |
| 5,573,950 | A | 11/1996 | Graessle et al. |
| 5,744,322 | A | 4/1998 | Krejcarek et al. |
| 5,863,754 | A | 1/1999 | Bajard |
| 6,027,691 | A * | 2/2000 | Watts ............... G01N 35/00594 422/64 |
| 6,632,661 | B2 | 10/2003 | Wickert |
| 7,298,885 | B2 | 11/2007 | Green et al. |
| 2002/0192742 | A1 | 12/2002 | Ushiyama et al. |
| 2004/0101189 | A1 | 5/2004 | Green et al. |
| 2004/0101951 | A1 | 5/2004 | Vent et al. |
| 2004/0101952 | A1 * | 5/2004 | Vent ................ G01N 15/1463 435/287.3 |
| 2004/0101954 | A1 | 5/2004 | Graessle et al. |
| 2004/0102903 | A1 | 5/2004 | Graessle et al. |
| 2005/0053265 | A1 | 3/2005 | Graessle et al. |
| 2005/0053266 | A1 | 3/2005 | Plumb et al. |
| 2005/0222778 | A1 | 10/2005 | Levinson et al. |
| 2006/0285539 | A1 | 12/2006 | Eden |

FOREIGN PATENT DOCUMENTS

| | | |
|---|---|---|
| EP | 0 088 601 | 9/1983 |
| EP | 0 301 600 | 2/1989 |
| EP | 0 397 256 | 11/1990 |
| EP | 0 429 030 | 5/1991 |
| EP | 0 547 709 | 6/1993 |
| FR | 2 602 074 | 1/1988 |
| GB | 2 227 346 | 7/1990 |
| JP | 57-63452 | 4/1982 |
| JP | 2-6729 | 1/1990 |
| JP | 09-117300 | 5/1997 |
| JP | 2001-157573 | 6/2001 |
| JP | 2006-507836 | 3/2006 |
| JP | 2009-291103 | 12/2009 |
| SU | 1434465 | 10/1988 |
| WO | WO 94/01528 | 1/1994 |
| WO | WO 94/26926 | 11/1994 |
| WO | WO 2004/051267 | 6/2004 |
| WO | WO 2005/009126 | 2/2005 |
| WO | WO 2006/014644 | 2/2006 |

OTHER PUBLICATIONS

Web-site page entitled "AID BacSpot Robot System: A Revolutionary New Tool for Fully Automated Colony Counting" from web site URL</www.aid-diagnostika.com>; 2006; AID Diagnostika.

Brochure entitled "AID Products and services overview"; from Autoimmun Diagnostika GmbH; printed 2007 (5 pgs).

Web-site page entitled "BIOTOOL SWISS innovative laboratory technology—Petriswiss PS 900 Serie" from Bio Tool AG; 2007; (2 pgs).

Brochure entitled "Petriswiss PS 900 P—Professional high throughput system" from BIOTOOL AG; 2006; (3 pgs).

Brochure entitled "Spiral Plater—Accelerated Bacterial Colony Enumeration" from Topac Inc.; 1999-2002; (3 pgs).

* cited by examiner

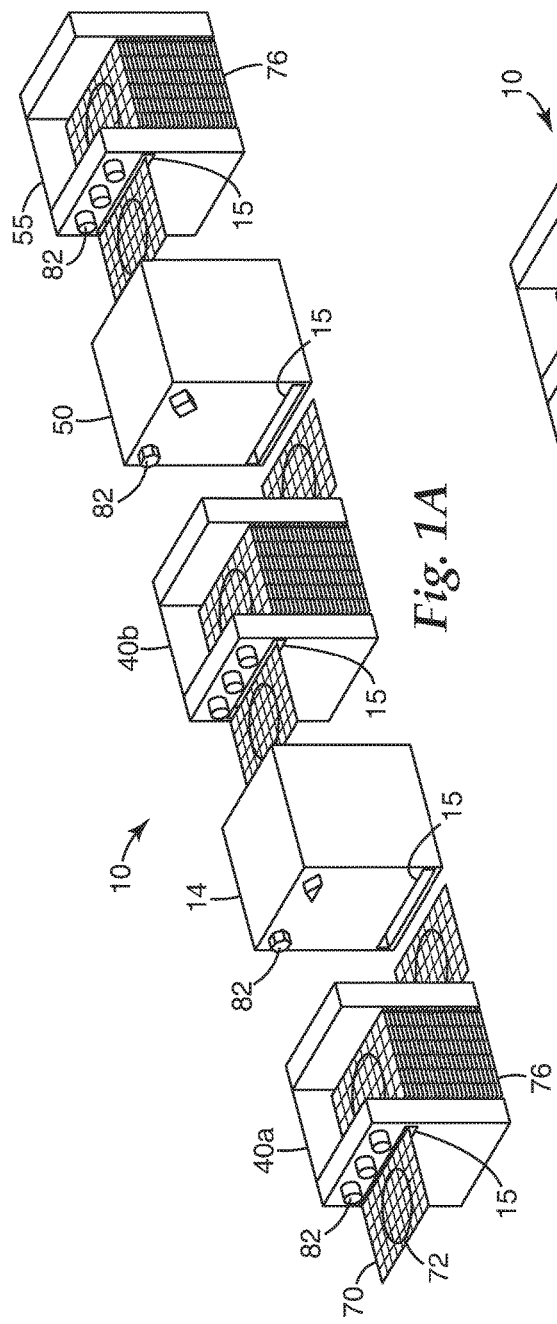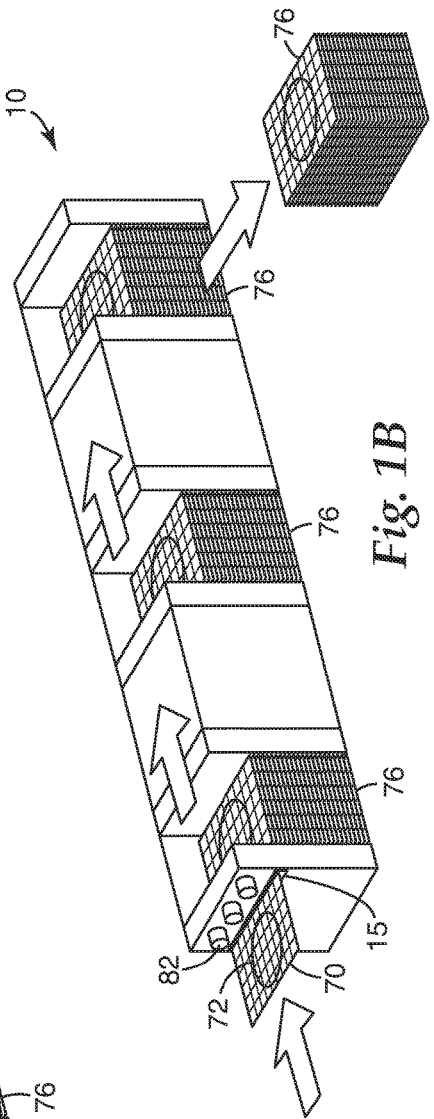

MODULAR SYSTEM AND METHOD FOR DETECTING MICROORGANISMS

CROSS REFERENCE TO RELATED APPLICATION

This application is a division of U.S. patent application Ser. No. 12/668,092, filed Mar. 7, 2011, (now U.S. Pat. No. 9,834,748) which is a national stage filing under 35 U.S.C. 371 of PCT/US2008/69485, filed Jul. 9, 2008, which claims the benefit of U.S. Provisional Patent Application No. 61/018,669, filed on Jan. 2, 2008, and U.S. Provisional Patent Application No. 60/948,687, filed on Jul. 9, 2007, the disclosure of which are incorporated by reference in their entirety herein.

BACKGROUND

Biological safety is a paramount concern in modern society. Testing for biological contamination in foods or other materials has become an important and often mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

A wide variety of culture devices (e.g., petri dishes containing agar media) have been developed. As one example, thin film culture devices have been developed by 3M Company (hereafter "3M") of St. Paul, Minn. Thin film culture devices are sold by 3M under the trade name PETRIFILM plates. Thin film culture devices can be utilized to facilitate the rapid growth and detection of bacteria or other biological agents including, for example, aerobic bacteria, *E. coli*, coliform, enterobacteriaceae, yeast, mold, *Staphylococcus aureus, Listeria, Campylobacter*, and the like. The use of PETRIFILM plates, or other growth media, can simplify bacterial testing of food samples.

Culture devices can be used to enumerate or identify the presence of bacteria so that corrective measures can be performed (in the case of food testing) or proper diagnosis can be made (in the case of medical use). In other applications, culture devices may be used to rapidly grow bacteria or other biological agents in laboratory samples, e.g., for experimental purposes.

Automated counting systems are also known. They can be separated into two basic categories. The first category includes those systems employing cameras or video equipment in conjunction with hard-wired circuits or digital computers to count the number of colonies in a petri dish. Examples of such systems are described in EP Publication No. 0 301 600; U.S. Pat. No. 3,811,036 to Perry; and French Publication No. 2 602 074.

Video-based systems suffer from a number of disadvantages. The primary disadvantage is the expensive and sophisticated equipment used in such systems to process the raw pixel image produced by the video cameras. To avoid multiple counting of the same colonies such systems typically include processing-intensive labeling schemes requiring relatively powerful computer systems to accurately count of the number of colonies in an acceptable amount of time.

An additional disadvantage is that many of these video-based systems require that the petri dishes be illuminated through their bottom surface which requires a substrate which is light permeable to ensure accurate counting. In other systems, such as that described in EP 0 301 600, the absorbance and transmission of light is used to detect colonies.

The second category of automated counting systems typically uses an array of photodetectors and hard-wired circuitry to perform the counting process. As with most of the video-based systems, the counting systems using photodetectors are also limited by the requirement that the petri dish be illuminated through its substrate to produce an accurate count. As a result, the substrate on which the colonies are contained must be light permeable, which is a particular problem with disposable culturing devices such as PETRIFILM. Examples of such systems are disclosed in U.S. Pat. No. 3,493,772 to Daughters II et al. as well as U.S. Pat. No. 3,736,432 to Sweet.

U.S. Patent Application Publication No. 2005/0053265 by Graessle et al. and U.S. Pat. No. 5,403,722 by Floeder et al. describe a method and apparatus for counting the number of microorganism colonies present on culture devices, such as PETRIFILM.

A need still exists for flexibility and automation in the use of culture devices for detection of microorganisms.

SUMMARY

The present invention relates to a modular sample processing and/or detection system that can be used to process samples to detect microorganisms. The system described herein provide a modular approach for automating many of the labor intensive steps associated with detection of microorganisms in a culture device, such as collection of multiple samples, sample loading, sample preparation, sample incubation, and detection of microorganisms in samples. Use of an automated modular integrated system for detection of microorganisms in culture devices facilitates consistent application of sample protocol, inhibits unintended preparation and use of the culture devices, and simplifies the user's interactions with samples during processing and detection of microorganisms using culture devices. As used herein, "modular system" means a system that includes two or more self-contained units or sections (e.g., process modules) wherein each process module performs at least one step or function associated with detection of microorganisms in a culture device, such as collection of multiple samples, sample loading, sample preparation (including sample dilution), sample incubation, and detection of microorganisms in samples.

The modular sample processing and/or detection system described herein can provide a user with the flexibility to customize a modular system in view of a variety of factors. Generally, the modular sample processing and/or detection system includes at least two process modules. The modules are aligned to provide transfer of a material (e.g., a sample or a culture device) between the modules. In a preferred embodiment, the modules include interlocking features that ensure alignment of the modules and minimize processing error by a user.

Among the potential advantages of the present invention is the ability of the customer to assemble different process modules within a given system. The different process modules may contain different modules to perform different functions on the same sample materials or a variety of sample materials. As a result, a single modular sample processing and/or detection system can be used to perform a variety of different tests and may include a quality control module capable of providing feedback to the user as to the accuracy of the processes run using the module system.

Furthermore, only process modules that are needed may be used, offering potentially significant savings for the user—especially if the process modules are preloaded with materials that would otherwise be wasted if provided in a conventional device. If fewer process modules are needed for a given sample preparation and/or detection system, the remainder of the modules may be removed to use only the minimum number of modules desired by the user.

The modular sample processing and/or detection system described herein can be designed for processing sample materials that include chemical and/or biological mixtures in a liquid, solid or gaseous form.

In one aspect, a modular system for detecting microorganisms is provided, the system comprising at least two modules, wherein each module performs at least one step in the process of detecting the microorganism, and a culture device, wherein the modules are aligned to allow for transfer of the culture device from one module to another.

In another aspect, a modular system for detecting microorganisms is provided, the system comprising at least two modules, wherein each module performs at least one step in the process of detecting the microorganism, and a culture device, and interlocking features to align the modules for transfer of the culture device from one module to another.

In a further aspect, a modular system for detecting microorganisms is provided, the system comprising at least two modules, wherein each module performs at least one step in the process of detecting the microorganism, and a plurality of culture devices, wherein at least one module comprises a means for detecting the microorganism on the culture device and at least one module comprises a means for collecting the plurality of culture devices.

A module for processing and/or detecting a microorganism is also provided, the module comprising a housing, a first slot formed in a first side of the housing for receiving a culture device, a second slot formed in a second side of the housing for ejecting the culture device following the performance of a processing step in the module, and interlocking features to align the module to with another module.

In another aspect, a method for detecting a microorganism is provided, the method comprising providing at least two modules, the module comprising a housing, a first slot formed in a first side of the housing for receiving a culture device, a second slot formed in a second side of the housing for ejecting the culture device following the performance of a processing step in the module and interlocking features to align the module to with another module; feeding a culture device into at least one of the modules, and detecting the microorganism in the culture device in at least one of the modules.

In another aspect, a modular system for detecting a microorganism in a sample is provided, the system comprising first and second modules aligned to allow for the transfer of liquid samples from the first module to the second module, a liquid sample, at least one sample reservoir unit, and a culture device. Each of the first and second modules performs at least one step in the process of preparing the sample to detect the microorganism. The first module is configured to hold at least two sample reservoir units. The second module is configured to transfer the liquid sample from the at least one sample reservoir unit to the culture device.

In another aspect, a modular system for detecting a microorganism in a sample is provided, the system comprising a culture device, a data processor to use analysis information to determine whether one or more conditions exist in the culture device, and a module to provide the analysis information for the data processor. The module comprises a housing which includes a detector for analyzing the culture device and providing analysis information (for the data processor), a first slot formed in a first side of the housing for receiving the culture device, a second slot formed in the housing for ejecting the culture device from the housing when the one or more conditions are present in the culture device, and a third slot formed in the housing for ejecting the culture device from the housing when one or more conditions are not present in the culture device.

In another aspect, a modular system for processing and/or detecting a microorganism in a sample is provided, the system comprising a culture device, a first module configured to hold a sample reservoir unit comprising a liquid sample, a second module configured to transfer the liquid sample to the culture device, a third module comprising a housing and a detector, and interlocking features to align two or more of the foregoing modules. The third module includes a first slot formed in the housing for receiving the culture device and a second slot formed in the housing for ejecting the culture device from the housing.

In another aspect, a method for detecting a microorganism is provided, the method comprising providing a culture device, a liquid sample, and at least two modules selected from a first module configured to hold at least two sample reservoir units, a second module configured to transfer the liquid sample to the culture device, and a third module comprising a housing and a detector. The third module further comprises a first slot is formed in the housing for receiving the culture device and a second slot is formed in the housing for ejecting the culture device from the housing. The method further comprises detecting the microorganism in the culture device in at least one of the modules.

In another aspect, a method for detecting a microorganism is provided, the method comprising providing a culture device, a liquid sample, a data processor which uses analysis information to determine whether one or more conditions exist, and at least two modules. A first module comprises a detector for analyzing the culture device and providing analysis information. The housing comprises a first slot formed in the housing for receiving the culture device, a second slot formed in the housing for ejecting the culture device from the housing if one or more conditions exist, and a third slot formed in the housing for ejecting the culture device from the housing if the one or more conditions do not exist. The method further comprises detecting the microorganism in the culture device, using the data processor to determine whether the one or more conditions exist in the culture device, and ejecting the culture device from the second slot if the one or more conditions exist. Optionally, the method further comprises ejecting the culture device form the third slot if the one or more conditions do not exist.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a reader that comprises "an" internal processor can be interpreted to mean that the reader can include "one or more" internal processors.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

FIG. 1A is an exploded perspective view of an automated modular apparatus and system according to one embodiment of the invention.

FIG. 1B is a perspective view of the assembled modular system of FIG. 1A.

DETAILED DESCRIPTION

Figure 2:
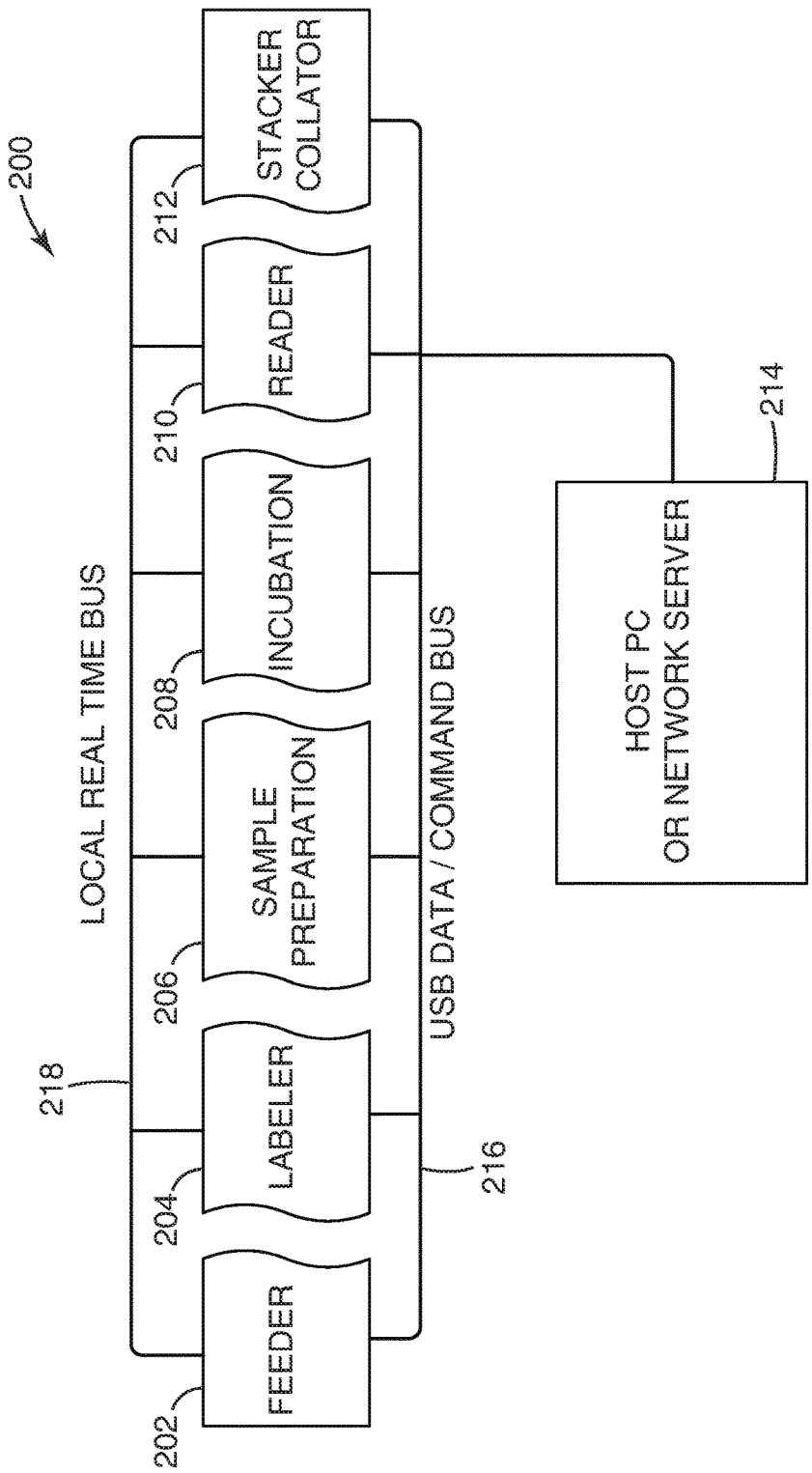
FIG. 2 is a block diagram of an exemplary modular system comprising a modular system coupled to an external computer.

In the following description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Although relative positional terms such as "top", "bottom", "above", "below", etc. may be used in connection with the present invention, it should be understood that those terms are used in their relative sense only. For example, when used in connection with the apparatus of the present invention, "top" and "bottom" may be used to signify opposing major sides of the apparatus and their modules. In actual use, elements described as "top" or "bottom" may be found in any orientation or location and should not be considered as limiting the apparatus and methods to any particular orientation or location. For example, the top surface of the sample processing and/or detection module may actually be located below the bottom surface of the sample processing and/or detection module during operation (although the top surface would still be found on the opposite side of the sample processing and/or detection module from the bottom surface).

Preferred embodiments of the invention include an interconnected, modular, and scaleable chain of functional modules which perform specific processes for detection of a microorganism on a culture device, such as PETRIFILM. The modular system described herein allows the user to pick functional steps of the sample protocol to be automated. This decision could be made based on several factors such as sample throughput, cost per test, protocol complexity and consistency, and space. Assembly and replacement of modules can be performed by the user in the field, as each module is preferable of a size that can be easily manipulated.

Various aspects of the invention may provide a number of advantages. For example, the invention may ensure that a culture device can be inserted into multiple modules that each perform a function in analyzing a sample for a microorganism of interest in a culture device. One or more samples may be collected, prepared for analysis, incubated, imaged or otherwise scanned to identify or enumerate amounts of biological agents, and then collated in an automated fashion. In particular, the modular configurations described herein can automate the insertion and positioning of culture devices in a manner that ensures that reliable processing of the sample can occur, thereby improving the integrity of automated scanning of such culture devices. Automation of the can also simplify the process for a user.

Various aspects of the invention may be useful with a variety of culture devices. For example, the invention may be useful with different plate-like devices for growing biological agents to enable detection and/or enumeration of the agents, such as thin-film culture plate devices, Petri dish culture plate devices, and the like. Therefore, the term "culture device" will be used broadly herein to refer to a medium suitable to permit detection and/or enumeration of biological agents. Many types of media could also be used in accordance with the invention.

Modular Systems

One embodiment of a modular sample processing and/or detection system 10 is depicted in FIGS. 1A and 1B. FIG. 1A is an exploded perspective view of a modular system 10 in accordance with one embodiment of the invention. As illustrated, modular system 10 comprises a first automated loading module 40a, a modular incubator 14, a second automated loading module 40b, an automated reader 50, and a collator 55.

In one embodiment, a module for loading multiple culture devices is provided to facilitate processing and analysis of culture devices 70. Culture device 70 may comprise a nutrient medium 72, in which certain microorganisms can be grown and which is shown as generally circular area in FIG. 1A. The automated loading module 40a is configured to collect multiple culture devices 70 and load the media into a subsequent module aligned with the automated loading module 40a. In FIG. 1, the automated loading module 40a is aligned with and loads the culture devices into modular incubator 14. Alternatively, the automated loading module 40a may load the culture devices sequentially into another module, such as the reader 50.

In a preferred embodiment, automated loading module 40a accepts a plurality of culture devices 70 loaded by the user to form a stack 76. The automated loading module 40a feeds individual culture devices 70 at a required time by the automation system to maintain maximum throughput. The automated loading module 40a temporally isolates the users' activities from the automated modular system 10 activities. Optimally, the automated loading module 40a ensures correct orientation and consistency for insertion of culture device 70 into other modules of the modular system 10.

The automated loading module 40a allows a user to load additional culture devices 70 without disrupting downstream automation of sample processing and/or detection steps in one or more downstream modules. As an illustration, automated loading module 40a could function as a top load, bottom feed, vertically-stacked module.

In an alternate embodiment, the biological stack can be loaded as a cartridge (not shown) that holds multiple culture devices 70. The cartridge could further facilitate automation of culture device 70 relative to feeding, incubating, or other process modules. For an exemplary description of a cartridge, see e.g. U.S. Pat. Nos. 5,573,950 and 5,744,322.

Automated loading module 40a includes a housing and input slot 15 for loading the culture device 70. As shown in FIG. 1A, each module includes a housing that defines an input slot 15 for receiving culture device 70. A guide mechanism may also be formed in each module to aid insertion and transfer of culture device 70 into and between modules. The module also includes an ejection slot (not shown), through which culture device 70 is ejected either into another module or out of the modular system 10. For example, various motorized rollers can grasp the culture device and draw the culture device into the various modules. Other types of transport mechanisms could also be used, however, instead of rollers.

It should be understood that the housing of a module may be manufactured of any suitable material or materials. Examples of suitable materials may include, e.g., polymeric materials (e.g., polypropylene, polyester, polycarbonate, polyethylene, etc.), metals (e.g., metal foils), etc. It may be preferred that the materials selected for the housing of the module exhibit good barrier properties for selected environmental conditions, such as prevention of exposure to air, water, and/or other microorganisms, etc. Other examples of suitable construction techniques/materials that may be adapted for use in connection with the process modules of the present invention may be described in, e.g., U.S. Pat. No. 7,298,885; U.S. Patent Application Publication No. 2005/0053265 (Graessle et al); U.S. Patent Application Publication No. 2006/0285539 (Eden); and U.S. Pat. No. 5,403,722.

As shown in FIGS. 1A and 1B, the automated loading module 40a feeds culture device 70 into modular incubator 14. Culture device 70 is fed into the modular incubator 14 from automated loading module 40a through bottom input slot 15. Modular incubator 14 performs incubation of the culture device 70 suitable for efficient biological growth, optimally with one or more isolated temperature controlled compartments within the modular incubator 14.

As shown in FIG. 1A, modular incubator 14 dispenses culture device 70 into a second automated loading module 40b. Second automated loading module 40b can be identical to and perform the same function as automated loading module 40a. Alternatively, the modular incubator 14 can feed culture device 70 into another module, such as reader 50 described below.

Second automated loading module 40b feeds culture device 70 to a reader 50 for detecting a microorganism in the culture device 70. In a preferred embodiment, the reader 50 comprises a housing and detection device to detect a microorganism, if present, in the culture device 70 when the culture device is within the housing. The reader may further comprise a transport mechanism, such as motorized rollers, to draw the culture device 70 into the reader 50, and one or more sensors to detect when the culture device is drawn to a detection position within the reader 50. The sensors can control the processing flow through reader 50. The sensors may comprise optical sensors, or any other type of sensor capable of sensing a growth plate. Sensors in the reader 50 can further be arranged to facilitate sensing and positioning of the culture devices in a plurality of positions to scan different parts of the culture devices 70, such as the scanning positions described in U.S. Patent Application Publication No. 2005/0053265 by Graessle et al.

Sensors can be arranged in the reader 50 or other module to facilitate sensing and positioning of the culture device 70. For example, the sensor may be sensed to generate or record an image of indicia, such as a bar code, on the medium. The indicia may identify the plate or type of plate, the type of sample, and/or other indicia of the sample so that appropriate scanning and image processing routines can be selected. For example, different processing routines may be performed to count biological growth (e.g., colonies of microorganisms) on the culture device 70 based on the indicia.

In a preferred embodiment, reader 50 houses an imaging device, such as a 2-dimensional monochromatic camera for generating one or more images of an inserted culture device 70. In addition, reader 50 may house various illuminators for illuminating the front and back of culture device 70 during imaging. The illuminators can illuminate culture device 70 with one or more colors, and one or more images of culture device 70 can be generated and then analyzed to determine bacteria counts on nutrient medium 72 as described in, e.g., U.S. Pat. No. 7,298,885 and U.S. Patent Application Publication No. 2005/0053265 (Graessle et al). In some embodiments, reader 50 may process images of different culture devices according to different image processing profiles as described in U.S. Pat. No. 7,298,885 and U.S. Patent Application Publication No. 2005/0053265 (Graessle et al).

By way of example, culture device 70 may comprise a certain type of nutrient medium 72, as sold by 3M under the trade name PETRIFILM plates. Medium 72 can be utilized to facilitate the rapid growth and detection of bacteria or other biological agents commonly associated with food contamination, including, for example, aerobic bacteria, *E. coli*, coliform, enterobacteriaceae, yeast, mold, *Staphylococcus aureus, Listeria, Campylobacter*, or the like.

Reader 50 may also include other features, such as a display screen (not shown) to display the progress or results of analysis of the culture device to a user. Other features may include, for example, a hinged door may facilitate access to each module.

In some embodiments, reader 50 includes an internal processor for analyzing the detection results of culture device 70. In other embodiments, however, the processing of images occurs external to reader 50, e.g., in a desktop computer, workstation, or the like as further described below in reference to FIGS. 2, 3A and 3B. In the latter case, reader 50 may include an interface to allow reader 50 to be communicatively coupled to another computer.

Referring again to FIGS. 1A and 1B, the reader 50 feeds culture devices 70 into collator 55 when the detection step in reader 50 is complete. Collator 55 organizes culture devices 70 after the detection step is performed in the one or more modules, such as reader 50, provided for that function. A user can set sorting criteria for collation of the culture devices 70 into collated stack 76. Examples of sort criteria could be origin of sample, medium plate type, CFU enumeration ranges, date of test, number of media, etc.

In the transfer of culture devices between modules, features may be included to facilitate transfer between the modules and/or maintain the integrity of the culture devices 70 from undesirable environmental conditions. In a preferred embodiment as shown in FIG. 1, the modules are designed with interlocking features 82. The interlocking features 82 may be mechanical, electrical or optical. Preferably, the interlocking features 82 provide a specific configuration for the user to interlock the modules during use that prevents incorrect alignment of the modules.

By way of example, mechanical interlocking features 82 include formed projections that project from the surface of the module housing, designed to align with the corresponding indention of matching shape in another module. Although shown in FIGS. 1A and 1B as triangular, hexagonal, and circular projections, one skilled in the art can use any form on projection that can provide a mating shape with the indention of the corresponding separate module. In an alternate embodiment, the interlocking features may mate by recognition of a particular optical or electrical signal.

Interlocking features 82 facilitate connection of compatible modules, alignment, and transport of the culture device. In a preferred embodiment, the interlocking features align the modules in a predetermined sequential order for use, preventing a user from configuring the modules that prevents or inhibits the sample processing or detection. As an illustration, FIG. 1B is a perspective view of the modular system 10 in FIG. 1 with the automated loading module 40a, modular incubator 14, a second automated loading module 40b, an automated reader 50, and a collator 55 aligned with the interlocking features 82 between the respective modules.

As discussed herein, each of the process modules preferably include process chambers that are adapted to retain the culture device 70 while one or more processes are performed on or using the sample materials. Examples of some potential processes that may be performed include collection of multiple samples, sample loading, sample preparation, sample incubation, and detection of microorganisms in samples.

In some instances, the modules may be designed for reuse with different process modules. In other instances, the modules may be designed for disposal after a single use. The attachment of process modules may, in some instances, be permanent—i.e., require destruction of some portion of the process module to separate the same after use, such as interlocking features 82.

FIG. 2 is a block diagram of an exemplary modular system 200 comprising automated feeder module 202, modular labeler 204, sample preparation module 206, incubation module 208, an automated reader module 210, and a stacker/collator 212. Feeder module 202 can function as described above in reference to automated loading module 40a of FIGS. 1A and 1B. Similarly, incubation module can function as described above in reference to module incubator 14; automated reader module 210 can function as described above in reference to reader 50; and stacker/collator 212 can function as described above in reference to collator 55; all in FIGS. 1A and 1B.

FIG. 2 additionally includes a modular labeler 204 that can read, add or otherwise process indicia that are either added to the culture device 70, or provided on the culture device 70 to the modular system 200.

A sample preparation module 206 is also provided. The sample preparation module can function to prepare the nutrient medium 72 on culture devices 70. Functions for sample preparation include combining and manipulating the sample, as well as inoculation and distribution of the sample on the nutrient medium 72. Functions provided in the sample preparation module can be tailored to the specific preparatory steps necessary to perform detection of microorganisms on the culture device 70. The sample solution can be deposited and spread in conformance with culture device used.

FIG. 2 further comprises an external computer 214 which performs control of the process steps in one or more modules, and/or analysis of the detection data generated by the automated reader module 210. External computer 214 may include, for example, a microprocessor programmed for image analysis of culture device 70. External computer 214 may comprise a personal computer (PC), desktop computer, laptop computer, handheld computer, workstation, or the like. External computer 214 can perform functions such as maintaining system configuration, performance logs, and higher systems communications.

System 200 is coupled to external computer 214 via an interface 216/218. Interface 216/218, for example, may comprise a Universal Serial Bus (USB) interface, a Universal Serial Bus 2 (USB2) interface, an IEEE 1394 FireWire interface, a Small Computer System Interface (SCSI) interface, an Advance Technology Attachment (ATA) interface, a serial ATA interface, a Peripheral Component Interconnect (PCI) interface, a conventional serial or parallel interface, or the like. In a preferred embodiment, as shown in FIG. 2, system 200 communicates and self identifies on a real time local communication bus 218 to arbitrate time critical events such as intermodule transport of the culture device, and a command and data bus 216 operating from a host computer.

Figure 3A:
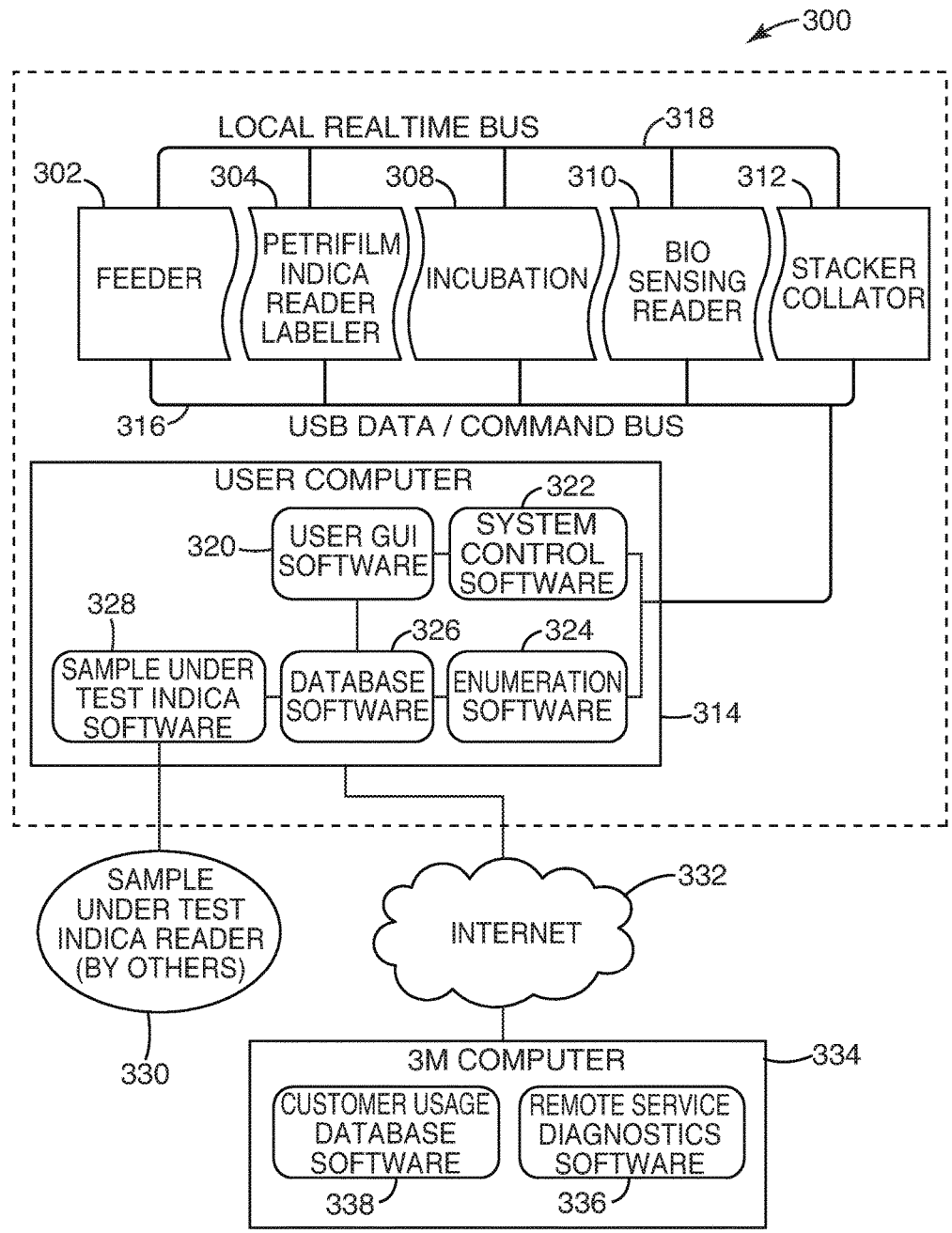
FIG. 3A is a block diagram of another exemplary modular system comprising a modular system coupled to an external computer.
Figure 3B:
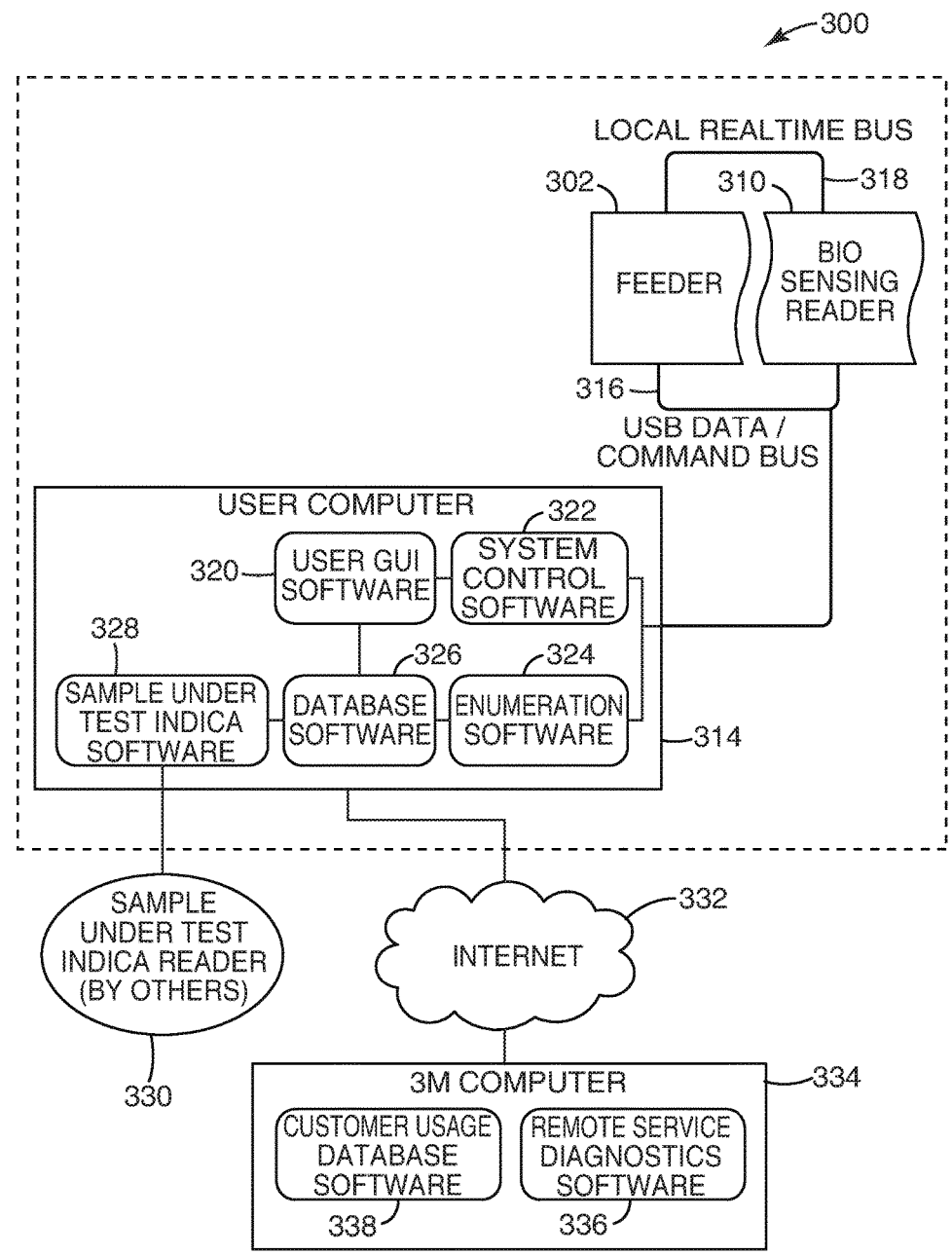
FIG. 3B is a block diagram of another exemplary modular system comprising a modular system coupled to an external computer.

FIGS. 3A and 3B are block diagrams of another exemplary modular system 300. In FIG. 3A, the modular system 300 comprises automated feeder module 302, modular labeler 304, incubation module 308, biosensing reader module 310, and a stacker/collator 312. Automated feeder module 302 can function as described above in reference to automated loading module 40a of FIGS. 1A and 1B. Similarly, incubation module can function as described above in reference to module incubator 14; automated reader module 302 can function as described above in reference to reader 50; and stacker/collator 212 can function as described above in reference to collator 55; all in FIGS. 1A and 1B.

FIG. 3A additionally includes a modular labeler 204 that can read, add or otherwise process indicia that are either added to the culture device 70, or provided on the culture device 70 processed in the modular system 300. FIG. 3B demonstrates an alternate modular system 300 with a minimized number of modules, comprising only automated feeder module 302, and biosensing reader module 310.

FIGS. 3A and 3B further comprise an external computer 314 which performs control of the process steps in one or more modules, and/or analysis of the detection data generated by the reader module 310. External computer 314 may include, for example, a microprocessor programmed for image analysis of culture device 70. External computer 314 may comprise a personal computer (PC), desktop computer, laptop computer, handheld computer, workstation, or the like. External computer 314 can perform functions such as maintaining system configuration, performance logs, and higher systems communications. Software for performance functions can be loaded on external computer 314, such as user software 320, system control software 322, sample under test indicia software (e.g., to recognize or otherwise indicate the source of a sample) which may be optionally read by sample under test indicia reader 330 external to system 300. Depending on the culture device and detection processes, external computer 314 may also include database software 326 and enumeration software 324.

System 300 is coupled to external computer 314 via interface 316/318. Interface 316/318, for example, may comprise a Universal Serial Bus (USB) interface, a Universal Serial Bus 2 (USB2) interface, an IEEE 1394 FireWire interface, a Small Computer System Interface (SCSI) interface, an Advance Technology Attachment (ATA) interface, a serial ATA interface, a Peripheral Component Interconnect (PCI) interface, a conventional serial or parallel interface, or the like. In a preferred embodiment, as shown in FIGS. 3A and 3B, system 300 communicates and self identifies on a real time local communication bus 318 to arbitrate time critical events such as intermodule transport of the culture device 70, and a command and data bus 316 operating from a host computer.

As shown in FIGS. 3A and 3B, internet connectivity 332 to a network server 334 can be used for remote servicing, reduced service cost, and monitoring customer usage trends (for example, plate types, usage patterns, and detecting unintended behavior, etc.) with customer usage software 338. Remote diagnostics 336 could be used to further control service costs as performance of the system could be monitored remotely to predict component failures and periodic maintenance such as cleaning. Operational changes including software updates could also be made remotely (for example, reflash firmware).

System 300 can be based on a limited distributed intelligence model. Enough control of system 300 can reside locally to the respective modules to enable local functions. Hierarchical control can be from external computer 314 and/or a network server 334 running a hosting application and graphical user interface. These applications can link by various known operating systems (e.g., dll, windows, etc.).

The present disclosure provides for modular systems for detecting a microorganism in a sample. The modular systems comprise individual modules which can form a system in which at least two modules, at least three modules, or at least four modules may be combined to process the sample and detect the microorganism. Any given module may be combined with any other module or modules to provide a system for processing a sample and/or detecting a microorganism.

Figure 4:
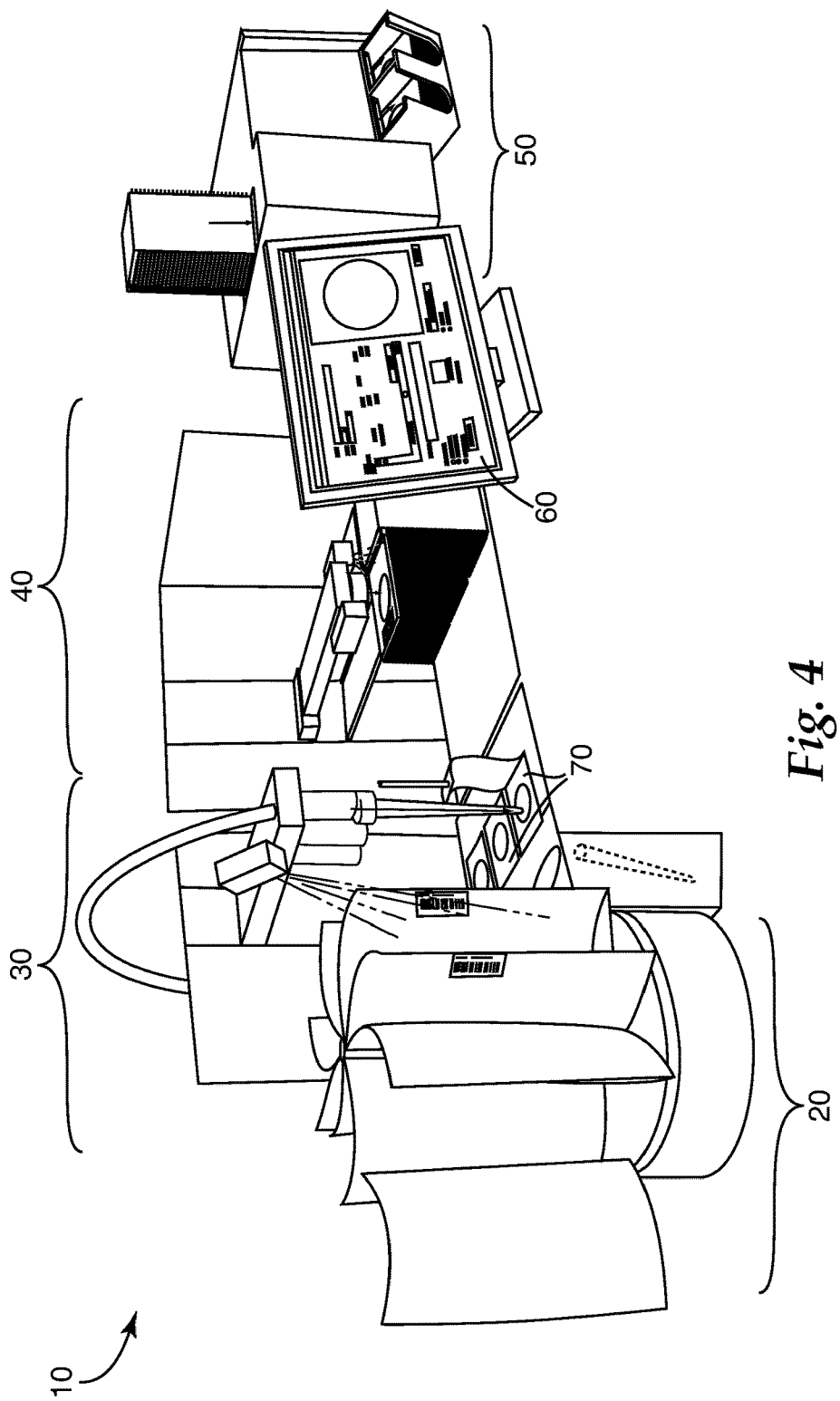
FIG. 4 is a perspective view of an automated modular apparatus and system according to one embodiment of the invention.

An embodiment of a modular sample processing and/or detection system 10 is depicted in FIG. 4. FIG. 4 is a perspective view of a modular system 10 in accordance with one embodiment of the invention. As illustrated, modular system 10 comprises sample reservoir module 20, liquid processing module 30, an automated loading module 40, a reader module 50, and an optional display 60. Culture devices 70 used with the modular system 10 are also shown in FIG. 4.

Figure 5:
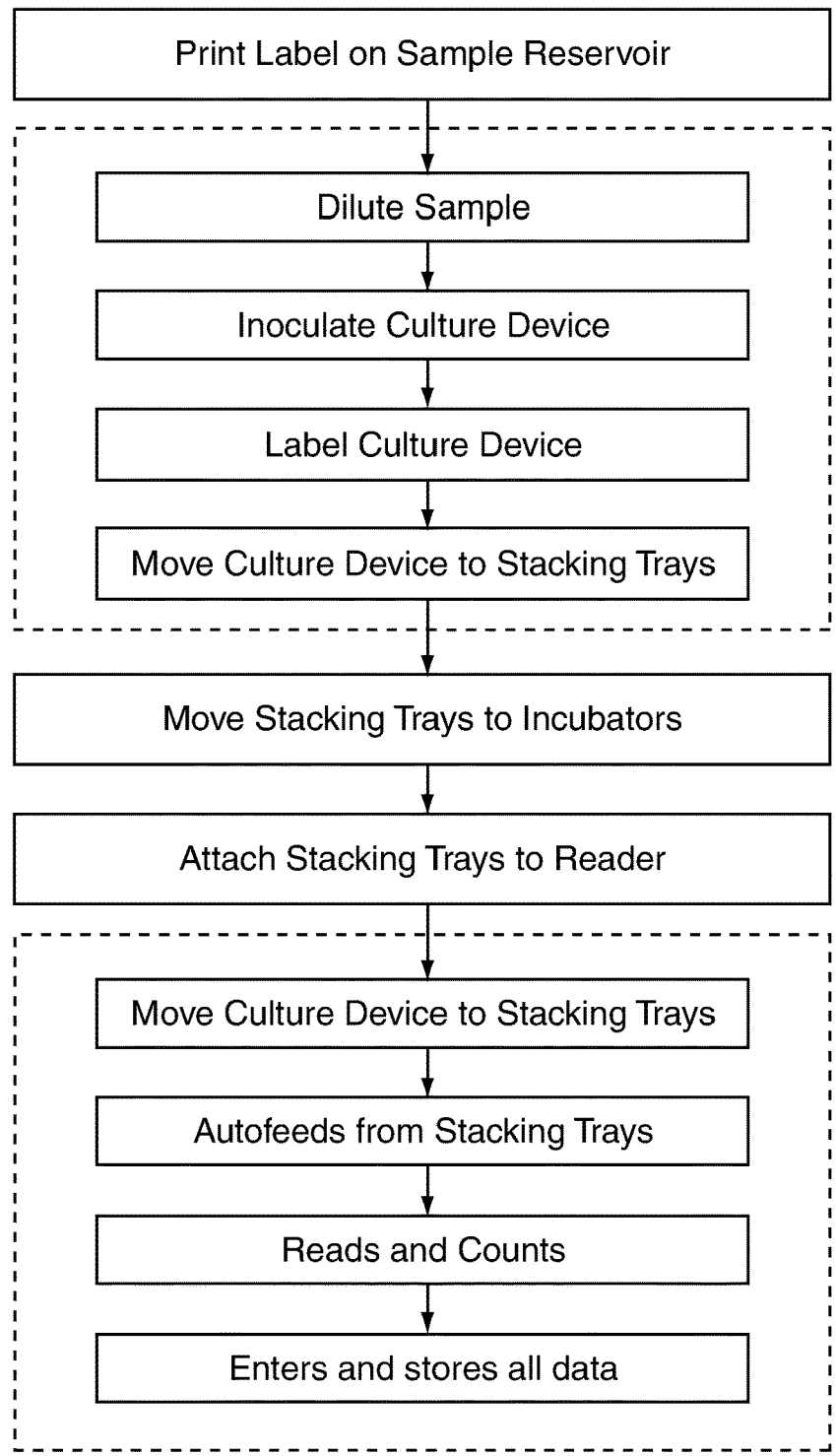
FIG. 5 is a block diagram of an exemplary process that can be used for the detection of a microorganism in a sample.

A modular system, such as the modular system 10 shown in FIG. 4, can be used to perform many steps in the process of preparing a sample and/or detecting a microorganism in the sample. FIG. 5 shows a block diagram of an exemplary process to prepare and analyze a sample for the presence of a microorganism. The process steps can include a) printing a label for a sample reservoir, b) optionally diluting a sample, c) inoculating a culture device with the sample or diluted sample, d) labeling a culture device, e) moving a culture device to a stacking tray, f) moving a stacking tray to an incubator, g) attaching a stacking tray to a reader, h) feeding a culture device from the stacking tray to the autoreader, i) reading a culture device and/or counting colonies in the culture device, j) entering and storing data from the autoreader into a data storage device, and k) sorting the culture devices as they are ejected from the autoreader. A modular system of the present invention can perform at least two, at least three, at least four, at least five, at least six, at least seven, at least eight, or at least nine of the foregoing process steps. The modular system of FIG. 4 can perform at a minimum the process steps that are enclosed in the two boxes shown by the dashed lines in FIG. 5.

In the transfer of culture devices 70 between modules, features (e.g., a protective cover, positive pressure, an air curtain) may be included to protect the modules and/or culture devices 70 from undesirable environmental conditions. As described above, the modules can be designed with interlocking features. The interlocking features may be mechanical, electrical or optical. Preferably, the interlocking features provide a specific configuration for the user to interlock the modules during use that prevents incorrect alignment of the modules.

By way of example, mechanical interlocking features include formed projections that project from the surface of the module housing, designed to align with the corresponding indention of matching shape in another module. Although shown in FIGS. 1A and 1B as triangular, hexagonal, and circular projections, one skilled in the art can use any form on projection that can provide a mating shape with the indention of the corresponding separate module. In an alternative embodiment, the interlocking features may mate by recognition of a particular optical or electrical signal.

Interlocking features facilitate connection of compatible modules, alignment, and transport of the culture device. In a preferred embodiment, the interlocking features align the modules in a predetermined sequential order for use, preventing a user from configuring the modules that prevents or inhibits the sample processing or detection.

As discussed herein, each of the process modules preferably include process chambers and/or surfaces that are adapted to retain the culture devices 70 while one or more processes are performed on such devices. Examples of some potential processes that may be performed include collection of multiple samples, sample loading, sample preparation, sample incubation, and detection of microorganisms in samples.

In some instances, the modules may be designed for reuse with different process modules. In other instances, the modules may be designed for disposal after a single use. The attachment of process modules may, in some instances, be permanent—i.e., require destruction of some portion of the process module to separate the same after use, such as interlocking features.

Samples

In certain embodiments, the fluid samples comprise a food or beverage. Methods for the preparation of food samples for microbiological analyses are well known. Some of the sample preparation methods for food samples involve suspending a known quantity of food material (25 grams, for example) in a relatively large volume of diluent (225 milliliters, for example). The sample is subjected to a strenuous mixing process, such as blending or stomaching, to create a relatively homogeneous liquid suspension. The samples are frequently processed in a plastic sample reservoir which is called a stomacher bag. Devices of the present disclosure provide a way to analyze food or beverage liquid samples; provided that the amount of suspended particulates or the viscosity of the sample will not significantly interfere with liquid transfer and/or microbial detection processes. Nonlimiting examples of foods which are routinely tested for microorganisms include meat (e.g., ground meat, poultry, fish, seafood), fresh or processed produce (e.g., fruit, vegetables), dairy (e.g., milk or milk products, whey, cheese), and beverages (e.g., milk, water, fruit juices, vegetable juices, tea).

In some embodiments, samples to be processed and analyzed include samples from a body of water. Nonlimiting examples of such bodies of water include surface water, water for human or animal consumption, and water used for industrial processes. Surface water includes an ocean, a lake, a river, a canal, a pond, a reservoir, a stream, and the like. Process water includes water that is used in municipal or industrial purposes, such as cleaning, washing, rinsing, cooling towers, water treatment holding tanks, and the like. Exemplary cleaning processes include food processing processes, such as, washing, rinsing, and disinfecting meat or produce for human or animal consumption.

In other embodiments, the devices and methods of this invention are used to collect and analyze any liquid sample that is amenable to processing and microbial detection such as, for example, solutions, mixtures, homogenates, or liquid suspensions of foodstuffs, beverages and pharmaceutical products. In certain embodiments, the liquid sample comprises one or more dissolved solute, such as sugars, salts, or proteins. In other embodiments, the liquid sample comprises one or more solvent, such as an alcohol, or a surfactant. Samples with solvents or surfactants can be used in accordance with the present invention, provided the solvents or surfactants do not significantly impair the liquid transfer and/or microbial detection. Preferably, the sample is substantially free of relatively large (e.g., greater than about 1 mm diameter) particulate materials that could clog sample processing equipment, such as a pipette tip.

In some embodiments, the devices and methods of the present disclosure can be used to process and detect microorganisms in an environmental or clinical sample. Typically, environmental or clinical samples are collected using a swab, a sponge, a wipe, or the like to collect residual material from a surface (e.g., a counter top, a floor, skin, a wound site) which may be contaminated with microorganisms. The collection device can be transferred to a sample reservoir, such as a stomacher bag, and mixed or homogenized with a solvent (e.g., Standard Methods Buffer, buffered peptone water, buffered saline, or distilled water) to release the microorganisms into the solvent. Subsequently, the solvent can be analyzed for the presence of a microorganism.

Individual liquid samples may contain almost any number and kind of microorganism. The number of microorganisms in a liquid sample may range from zero organisms per milliliter, in a sample that has been subjected to sterilizing conditions, up to approximately $10^9$ or more organisms per milliliter in a heavily-contaminated sample. The devices and methods of the present invention provide for the analysis of liquid samples containing a wide variety of bacterial concentrations.

Sample Reservoir Module

Figure 6:
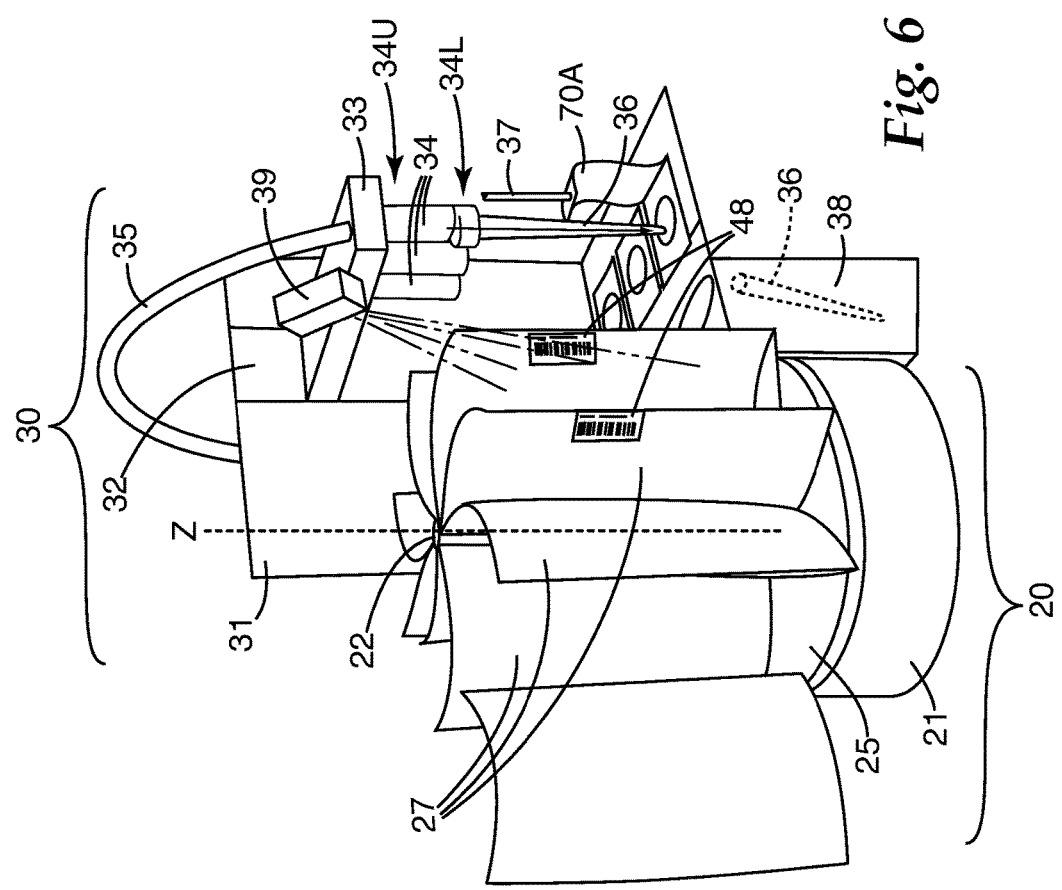
FIG. 6 is a perspective view of the sample reservoir module and the liquid processing module of the modular apparatus and system of FIG. 4.

FIG. 6 shows one embodiment of a sample reservoir module 20 in accordance with the present invention. The sample reservoir module 20 can include a base 21, to which a support rod 22 can be pivotably attached. The support rod 22 can be attached directly or indirectly to any of a number of drive mechanisms (not shown) known in the art (e.g., a belt drive, a chain drive, a gear drive, or a screw drive, or a liquid- or gas-driven impellor), which can provide the motive force to pivot the support rod 22 about axis Z, thereby changing the relative position of sample reservoirs 27. In an alternative embodiment, support rod 22 can be fixedly attached to base 21 and the base 21 can be attached directly or indirectly to a drive mechanism (not shown), which provides the motive force to pivot the base 21 around axis Z, thereby changing the relative position of sample reservoirs 27.

Sample reservoir module 20 can comprise an optional platform 25 to support the sample reservoirs 27. The platform 25 can provide a surface which bears the weight of the sample reservoirs 27 and can be particularly useful when the sample reservoirs 27 are constructed from materials that can stretch when loaded with a relatively heavy sample and/or a relatively large volume of sample-suspending solution.

Figure 7:
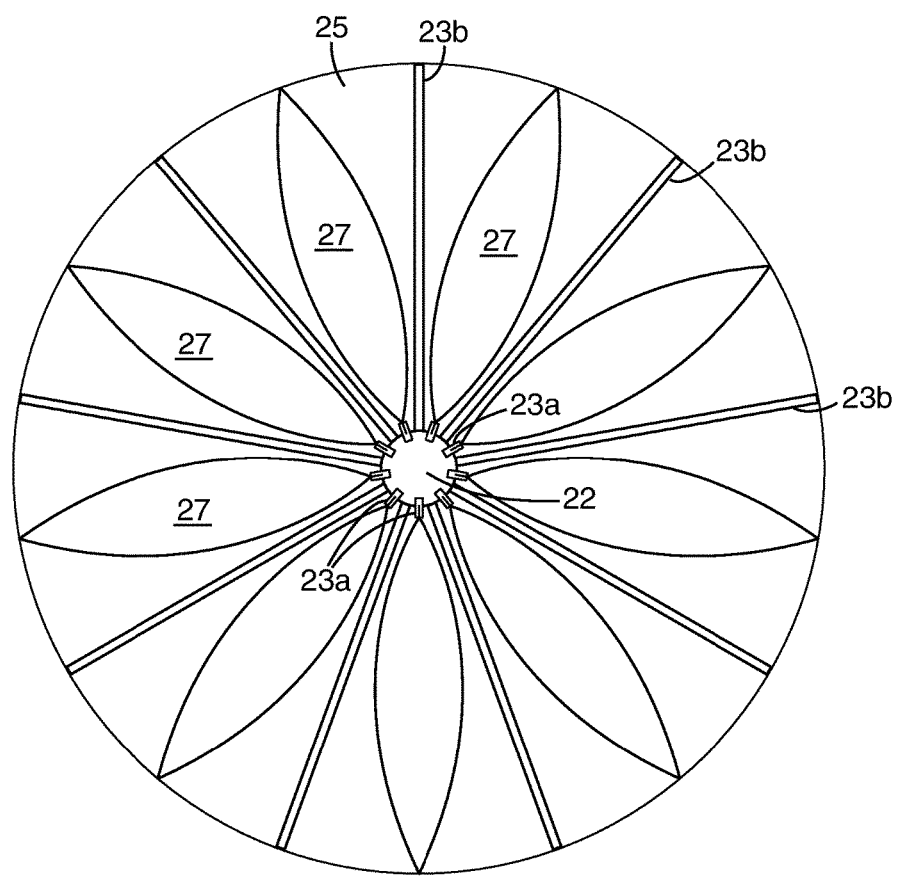
FIG. 7 is a top view of the sample reservoir module of FIG. 6.
Figure 8A:
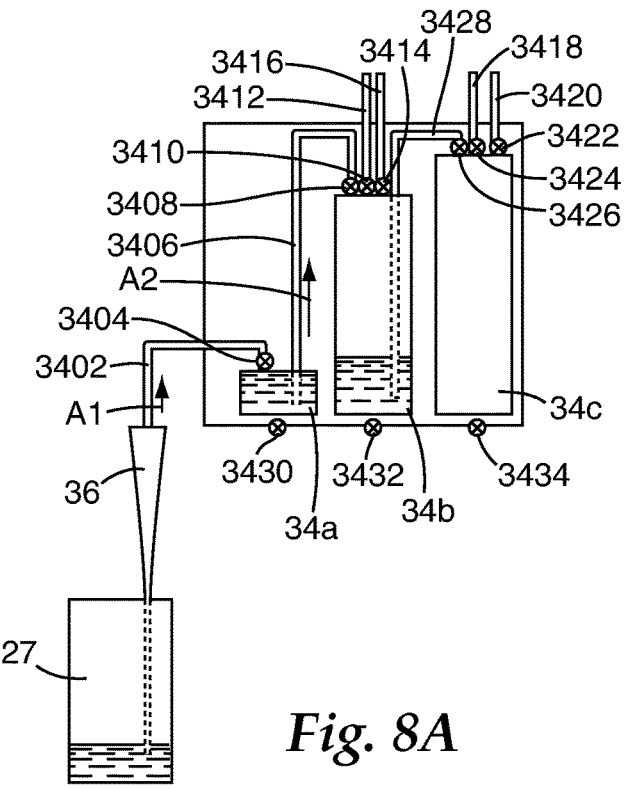
FIG. 8A-F is a cross-sectional view of the plurality of chambers of the liquid processing module of FIG. 6.
Figure 8B:
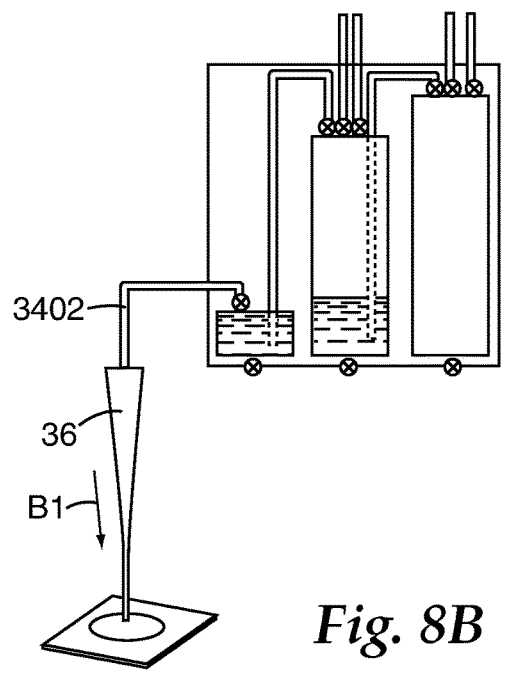
Figure 8C:
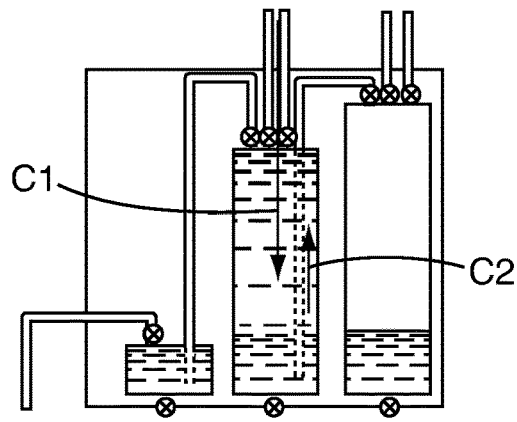
Figure 8D:
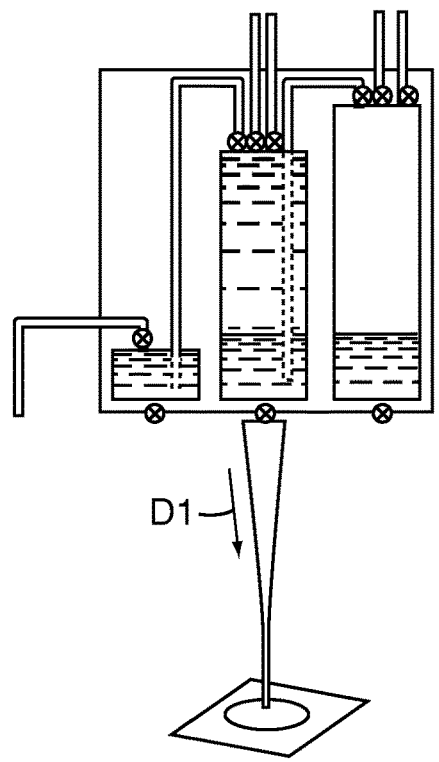
Figure 8E:
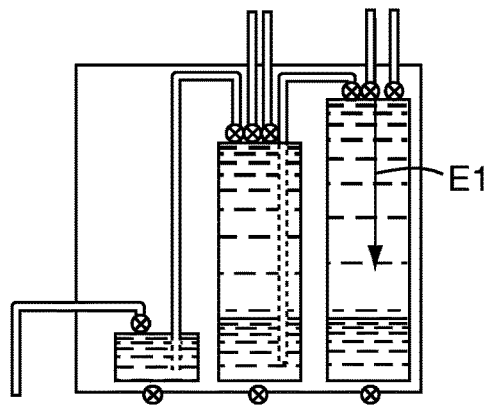
Figure 8F:
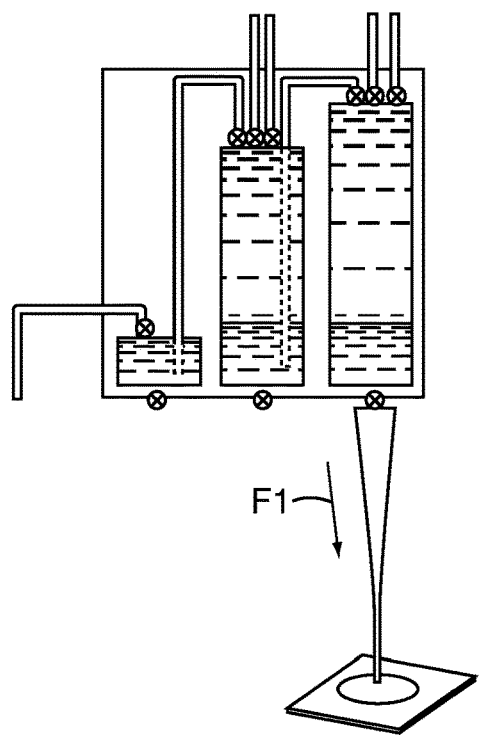

FIG. 7 shows a top view of an alternative embodiment of sample reservoir module 20. This illustrated embodiment further comprises optional spacers 23b, which can keep the sample reservoirs 27 spaced apart from each other and, in addition to the platform 25, may further support the bulk and/or weight of the sample reservoirs 27. FIG. 7 also shows platform 25, support rod 22, spacers 23b, and clips 23a, which grasp the sample reservoirs 27. Clip 23a should releasably grasp the sample reservoir 27 firmly enough to prevent unintentional release of the sample reservoir 27 from the clip 23a during normal use.

In the illustrated embodiment of FIG. 6, the sample reservoirs 27 comprise a plastic bag, such as a stomacher bag. The sample reservoirs 27 can be detachably attached to the support rod 22 via a number of various attachment means, such as clips 23a shown in FIG. 7. In some embodiments, each sample reservoir 27 can be detachably attached to the support rod 22 via individual attachment means. In an alternative embodiment, a plurality of sample reservoirs 27 can be detachably attached to the support rod 22 via a single attachment means. The attachment means 23a can comprise a variety of structures from which a sample reservoir 28 can be secured to the support rod 22. Nonlimiting examples of attachment means 23a include clamps, clips, spring clips, hooks, springs, magnets, and a vacuum source. Also shown in FIG. 6 is a sample indicium 48 which is affixed to sample reservoir 27. Sample indicium 48 can generate a recognition event that can be read by automated indicium reader 39 and may be produced in a number of different forms such as, for example, a printed indicium (e.g., an adhesive label, a barcode label, or a label printed directly onto the sample reservoir 27) which may be observed or imaged when illuminated with light (e.g., ultraviolet, visible, or infrared wavelengths); an embossed indicium; or a radio frequency indicium (e.g., RFID). In some embodiments, different processing routines (e.g., dilution schemes, number of replicate tests per sample, diluent used, type of culture device 70 used, etc.) may be performed to count biological growth on the culture device 70 based on the information provided by the indicium 48 detected on the culture device 70 by the indicium reader 39.

It should be understood that the components of the sample reservoir module 20 may be manufactured of any suitable material or materials. Examples of suitable materials may include, e.g., polymeric materials (e.g., polypropylene, polyester, polycarbonate, polyethylene, etc.), metals (e.g., metal foils), etc. It may be preferred that the materials selected for the components of the module exhibit good barrier properties for selected environmental conditions, such as resistance to degradation or contamination due to exposure to air, water, and/or other microorganisms, etc. It may be preferred that materials selected for moving parts exhibit good durability properties and/or compatibility with lubricants to reduce friction and degradation. A drive mechanism, if present, to pivot the base 21 and/or support rod 22, may be shielded from exposure to moisture or contamination than may occur when processing sample reservoirs 27. In certain preferred embodiments, the materials selected for the base 21, support rod 22, attachment means 23a, platform 25, and/or spacer 23b can have resistant properties, antimicrobial properties, or have coatings that are antimicrobial and/or resistant to degradation by materials or processes used for microbial decontamination such as, for example, steam sterilization, a solution of 70% isopropyl alcohol, or a solution of sodium hypochlorite.

Liquid Processing Module

FIG. 6 also shows an exemplary liquid processing module 30. Liquid processing module 30 comprises a housing 31, an elevator 32, a processing platform 33, cover lifter 37, an optional waste container 38, and an indicium reader 39. The illustrated embodiment shows indicium reader 39 attached to processing platform 33. In alternative embodiments, the indicium reader 39 can be attached at any location on the module (e.g., the housing 31) where it can be used to detect sample indicia 48 located on a sample reservoir 27.

Processing platform 33 can include a plurality of chambers 34 into which a liquid sample, a diluted liquid sample, and/or a liquid diluent can be transferred. In certain embodiments, the processing platform 33 can comprise a single chamber 34. External conduit 35 may be used to provide a liquid (e.g., a sample, a diluent, and/or a reagent), a gas (e.g., compressed air or nitrogen), or a vacuum to the processing platform 33. In alternative embodiments, said liquids, gasses, and/or vacuum may be provided to the processing platform through an internal conduit (not shown) which passes from the housing 31, through the processing platform 33, and into one or more of the chambers 34. Also shown in FIG. 6 is a culture device 70(A).

In FIG. 6, the processing platform 33 can be constructed to provide movement of the chambers 34, the indicium reader 39, and/or the tip 36 in one or more directions. Laboratory robots such as the type described in U.S. Pat. Nos. 5,646,069 and 6,027,691, which are hereby incorporated by reference in their entirety, teach exemplary mechanisms for providing three-dimensional movement for the processing platform 33. In some embodiments, the elevator 32 can provide for vertical movement of the processing platform 33. In other embodiments, the elevator 32 may provide for vertical movement and/or horizontal movements which are parallel to the face of the housing 31 from which the processing platform 33 extends. Movement of the processing platform 33 can facilitate, for example, scanning sample indicia 48, obtaining a liquid sample from the sample reservoir 27, depositing a used tip 36 or chamber 34 into the waste container 38, and/or obtaining a new tip 36 or chamber 34.

Chambers 34 comprise a hollow body, having an upper end 34U and a lower end 34L, with at least two distinct openings. The chambers 34 can be formed in various sizes and shapes, such as the cylindrical-shaped chambers shown in FIG. 7. The chambers 34 in FIG. 6 have an opening at the upper end 34U, which is in fluid communication with the conduit 35. As used herein, the term "fluid communication" means that a fluid, such as a liquid and/or a gas, may pass in either direction between chamber 34 and conduit 35 including, for example, the temporary removal of some or all of the air from chamber 34 to create a vacuum or the introduction of air (or gas) or pressurized air (or gas) into chamber 34 to expel the contents of the chamber 34. Chambers 34 can have an opening at the lower end 34L through which a liquid can be introduced and/or expelled. In some embodiments, a tip 36 (e.g., a pipette tip) can be attached in fluid communication with the opening in the lower end 34L of the chamber 34. In an alternative embodiment, the tip 36 may be an integral part of the chamber 34. The chamber 34 may have various liquid capacities. For example, the chamber 34 may have a liquid capacity of about 0.1 milliliters, about 0.5 milliliters, about 1 milliliter, about 2 milliliters, about 5 milliliters, about 10 milliliters, about 25 milliliters, about 50 milliliters or about 100 milliliters.

In some embodiments, processing platform 33 may comprise fluidic conduits (not shown) that allow for the passage of liquid from one chamber 34 to another. Such fluidic transfer components are described in, for example, U.S. Pat. Nos. 5,646,069 and 6,027,691. Thus, the fluidic components of the liquid processing module 30 with a plurality of chambers 34 can perform serial dilutions of a sample thereby providing separate chambers containing, for example, an undiluted sample, a 1:10-diluted sample, and a 1:100-diluted sample, respectively.

FIG. (8) shows a cross-sectional schematic view of one embodiment of chambers 34a-34c and the microfluidic components to provide for liquid processing (e.g., liquid transfer, dilution, reagent addition, etc.). Panel A of FIG. 8 shows detailed components that are either not included and/or not labeled in panels B-F to allow visualization of other features of the chambers 34a-34c and to allow visualization of the liquid transfer into and out of the chambers.

Panel A (FIG. 8) shows a sample reservoir 27 comprising a liquid sample, a tip 36, an intake conduit 3402, comprising a check valve 3404, a transfer conduit 3406 comprising a check valve 3408, an intake conduit 3412 comprising a check valve 3410, a vent 3414 comprising a check valve 3416, a transfer conduit 3428 comprising a check valve 3426, an intake conduit 3418 comprising a check valve 3424, and a vent 3420 comprising a check valve 3422. Intake conduits 3412 and 3418 can be in fluid communication with at least one liquid reservoir (not shown), a compressed air or gas source (not shown), and a vacuum source (not shown)

In panel A of FIG. 8, the liquid sample is drawn into chamber 34a (see arrow A1) by inserting tip 36 into liquid sample and applying a vacuum through intake conduit 3412 while check valves 3404, 3408, and 3410 are open and check valves 3416 and 3426 are closed. In the illustrated embodiment, chamber 34a is configured to hold 10 milliliters of sample and the vacuum source is controlled to withdraw 21 milliliters of sample volume from the sample reservoir 27. Accordingly, the excess 11 milliliters of sample is drawn through transfer conduit 3406 into chamber 34b (see arrow A2).

As shown in FIG. 8 panel B, a tip 36 is attached to chamber 34a. Check valves 3408, 3410, and 3430 are opened and check valves 3404, 3416 and 3426 are closed. Compressed air or gas is delivered through intake conduit 3412 to provide positive pressure to expel a volume of liquid (e.g., 1 milliliter) from chamber 34a into culture device 70 (see arrow B1).

In the next step, shown in panel C of FIG. 8, check valve 3408 is closed and check valves 3410, 3426, and 3422 are opened. A ninety-nine milliliter volume of liquid diluent is delivered (see arrow C1) through intake conduit 3412 and mixed with the sample in chamber 34b, which has a volumetric capacity of 99 milliliters. Accordingly, the excess 11 milliliters are transferred (see arrow C2) through transfer conduit 3428 into chamber 34c.

As shown in FIG. 8 panel D, a tip 36 is attached to chamber 34b. Check valves 3410 and 3432 are opened and check valves 3408 and 3416 are closed. Compressed air or gas is delivered through intake conduit 3412 to provide positive pressure to expel a volume (e.g., 1 milliliter) of liquid from chamber 34a into culture device 70 (see arrow D1).

In the next step, shown in panel E of FIG. 8, check valve 3426 is closed and check valves 3424 and 3422 are open. A ninety-nine milliliter volume of diluent is transferred through intake conduit 3418 into chamber 34c (see arrow E1), where it is mixed with the liquid sample.

As shown in FIG. 8 panel F, a tip 36 is attached to chamber 34c. In this example, check valves 3426 and 3422 would be closed and check valves 3424 and 3434 would be open. Compressed air or gas can be delivered through intake conduit 3418 to provide positive pressure to expel a volume (e.g., 1 milliliter) of liquid from chamber 34c into culture device 70 (see arrow F1).

It should be recognized that the fluidic components and volumes described in the aforementioned dilution process represent one example of many various liquid handling procedures that could be performed in the liquid handling module 30. In other embodiments, the volumes of liquid transferred could be smaller (e.g., an order of magnitude smaller). In other embodiments, the volumes of liquid transferred could be larger. It should also be recognized that an alternative embodiment can involve transferring undiluted sample to chambers 34a-34c, thereby providing the ability to deliver replicate undiluted sample to a plurality of culture devices 70. It should also be recognized that the intake conduits 3402, 3412, and 3418 could be used to transfer a liquid containing a reagent, such as a nutrient, an indicator, a stain, or the like into the chambers 34a-34c to mix with the sample.

Referring back to FIG. 6, after the liquid sample has been transferred (and, optionally diluted) to chamber 34, the entire liquid sample (or a portion thereof) can be distributed from the chamber 34 to the culture device 70 (i.e., the culture device 70 is inoculated). The cover lifter 37 can be used to open the culture device 70 to allow the liquid sample to be transferred to the interior of the culture device. The cover lifter 37 can lift the cover 70A of the culture device 70 by a variety of mechanisms. In certain embodiments, the cover lifter 37 may include a vacuum source (not shown) which, when actuated, can reversibly attach the cover 70A to the cover lifter 37. The cover lifter 37 can be subsequently raised to lift the cover 70A, thereby exposing the interior of culture device 70. After the liquid sample is distributed to the culture device 70, the cover 70A can be lowered and the vacuum can be released.

In an alternative embodiment, the cover lifter 37 can comprise an adhesive tip (not shown) which, when contacted with the cover 70A can reversibly attach to the cover 70A. The cover lifter 37 can be raised subsequently, thereby exposing the interior of the culture device 70. After the liquid sample has been distributed into the culture device 70, the cover lifter 37 can be raised to a point at which the adhesive bond with the cover 70A is broken. In this embodiment, it may be preferable to secure the culture device 70 to the liquid processing module 30 (e.g., by a vacuum) to facilitate separation of the cover lifter 37 from the cover 70A. Cover lifter 37 may also comprise a mechanical armature (not shown) which can be used to position the cover lifter 37 during the process of raising and lowering the cover 70A.

Stacking Tray Loading Module

Figure 9:
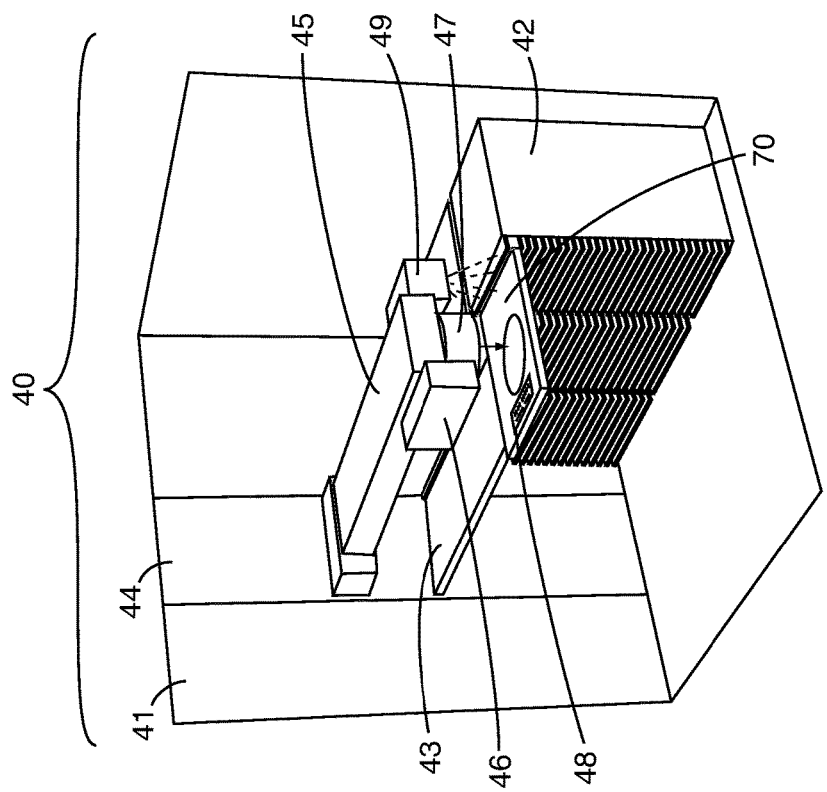
FIG. 9 is a perspective view of the stacking module of the modular apparatus and system of FIG. 6.

FIG. 9 shows one embodiment of an automated loading module 40 to facilitate processing and analysis of a plurality of culture devices 70. The automated loading module 40 is configured to collect multiple culture devices 70 and load the culture devices 70 into stacking trays 42. The automated loading module 40 can comprise a housing 41, a stacking tray 42, a stacker platform 43 which may be attached to an elevator 44, and a stacker processor 45 which may comprise a spreader 47, a labeler 46 and/or an indicium reader 49. In some embodiments, the stacker platform 43 can be attached to the elevator 44.

The stacker platform 43 can be used in conjunction with the liquid processing module 30 (FIG. 6) to hold the culture devices 70 during the inoculation step. For example, after the liquid sample has been deposited into a PETRIFILM-type culture device 70 in the liquid processing module 30, the stacker platform 43 can position the culture device 70 below the stacker processor 45 and the spreader 47 can be contacted with the culture device 70 to complete the inoculation. The stacker platform 43 can be subsequently moved in proximity to the labeler 46, where a sample idicium 48 can be applied, printed, or embossed onto the culture device 70. Indicium 48 can generate a recognition event that can be read by an automated indicium reader 49 and may be produced in a number of different forms such as, for example, a printed indicium (e.g., an adhesive label, a barcode label, or a label printed directly onto the culture device 70) which may be observed or imaged when illuminated with light (e.g., ultraviolet, visible, or infrared wavelengths); an embossed indicium; or a radio frequency indicium (e.g., RFID). In certain embodiments, the indicium 48 on the culture device 70 may include information which relates to, for example, the sample type, the diluent, the dilution factor, the date and time of inoculation, the type of culture device 70 (e.g., total aerobic count, coliform count, E. coli count, etc.), the operator, and/or any other information related to the sample, the test, the equipment, the culture devices 70, or the testing facility. In some embodiments, different processing routines may be performed to count biological growth on the culture device 70 based on the information provided by the indicium 48 detected on the culture device 70 by the indicium reader 49.

After the culture device 70 is labeled, the indicium 48 on culture device 70 may be read by indicium reader 49 prior to moving the culture devices into the stacking tray 42. In some embodiments, the indicium 48 on the culture device 70 is scanned by the indicium reader 49 as the culture device 70 is moved from the stacker platform 43 into the stacking tray 42. Movement of the culture devices 70 can be accomplished by movement of the stacker platform 43 on which the culture devices 70 can be positioned. Movements of the stacking platform 43 can be accomplished by a number of mechanical drive mechanisms known in the art, such as a gear drive, chain drive, belt drive, screw drive, or the like. The motive force for such movements may be provided by, for example, a motor (not shown) located in the housing 41.

Optimally, the stacker platform 43 ensures correct orientation and consistency of placement or positioning of culture devices 70 in other modules (e.g., the sample processing module) of the modular system and/or the stacking tray 42 in the automated loading module 40.

The automated loading module 40 allows a user to load additional culture devices 70 into a module without disrupting upstream automation of sample processing and/or detection steps in one or more downstream modules. As an illustration, the stacker platform 43 of automated loading module 40 could accept new (i.e., uninoculated) culture devices 70 from a top-fed or bottom-fed loading device (not shown) containing the new culture devices 70 or a cartridge-fed system, such as the system described in, for example, U.S. Pat. Nos. 5,573,950 and 5,744,322. After receiving the new culture devices 70, the stacker platform 43 can position the culture devices 70 for inoculation by, for example, the liquid processing module 30 of FIG. 6.

It should be understood that the housing 41 and other components of the automated loading module 40 may be manufactured of any suitable material or materials. Examples of suitable materials may include, e.g., polymeric materials (e.g., polypropylene, polyester, polycarbonate, polyethylene, etc.), metals (e.g., stainless steel, aluminum, metal foils), etc. It may be preferred that the materials selected for the housing of the module exhibit good barrier properties for selected environmental conditions, such as prevention of exposure to air, water, and/or other microorganisms, etc. It may be preferred that materials selected for moving parts exhibit good durability properties and/or compatibility with lubricants to reduce friction and degradation. Other examples of suitable construction techniques/materials that may be adapted for use in connection with the process modules of the present invention may be described in, e.g., U.S. Pat. No. 7,298,885; U.S. Patent Application Publication No. 2005/0053265 (Graessle et al); U.S. Patent Application Publication No. 2006/0285539 (Eden); and U.S. Pat. No. 5,403,722. A drive mechanism to provide for movement of the stacker platform 43, elevator 44, and/or stacker processor 45 may be shielded from exposure to moisture or contamination than may occur when processing sample reservoirs 27. In certain preferred embodiments, the materials selected for the housing 41, stacker platform 43, stacker processor 45, and/or stacking trays 42 can have resistant properties or have coatings that are resistant to degradation by materials or processes used for microbial decontamination such as, for example, steam, a solution of 70% isopropyl alcohol, or a solution of sodium hypochlorite.

Figure 10:
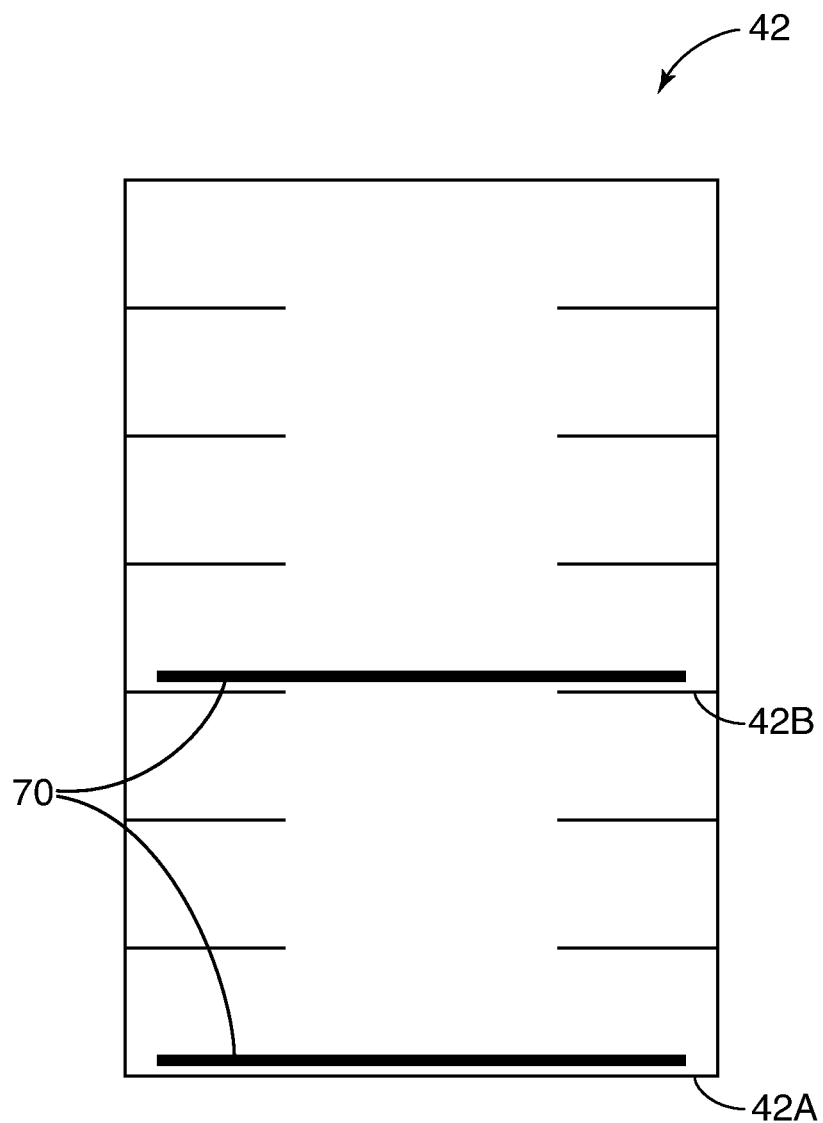
FIG. 10 is a front view of a stacking tray in accordance with the stacking module of FIG. 4.

FIG. 10 shows a front view of one embodiment of a stacking tray 42. As shown, the stacking trays 42 can possess at least one shelf, and preferably, a plurality of shelves on which a culture device 70 can be placed. In this embodiment, the bottom shelf 42A can provide for continuous contact across the entire width of a culture device 70. Alternatively, the shelf can provide partial contact across the width of culture device 70, as shown by shelf 42B in FIG. 10. The shelves 42A can be spaced apart to hold a least one, at least two, at least 3 at least 4, at least 5, at least 10, at least 15, or at least 20 culture devices 70. Advantageously, the shelves 42A can provide air spaces between culture devices 70 or stacks of culture devices 70, which can facilitate heat transfer and rapid temperature equilibration when the stacking trays 42 are placed into an incubator. In certain embodiments, the stacking trays 42 may be constructed from heat-conducting materials, such as aluminum, to further facilitate rapid temperature equilibration of the culture devices 70.

Sensors (not shown) can be arranged in the liquid processing module 30, the automated loading module 40, or other modules to facilitate sensing and positioning of the culture devices 70. For example, the sensor may be used to generate or record an image of indicia, such as a bar code, on the medium.

Reader Module

Figure 11:
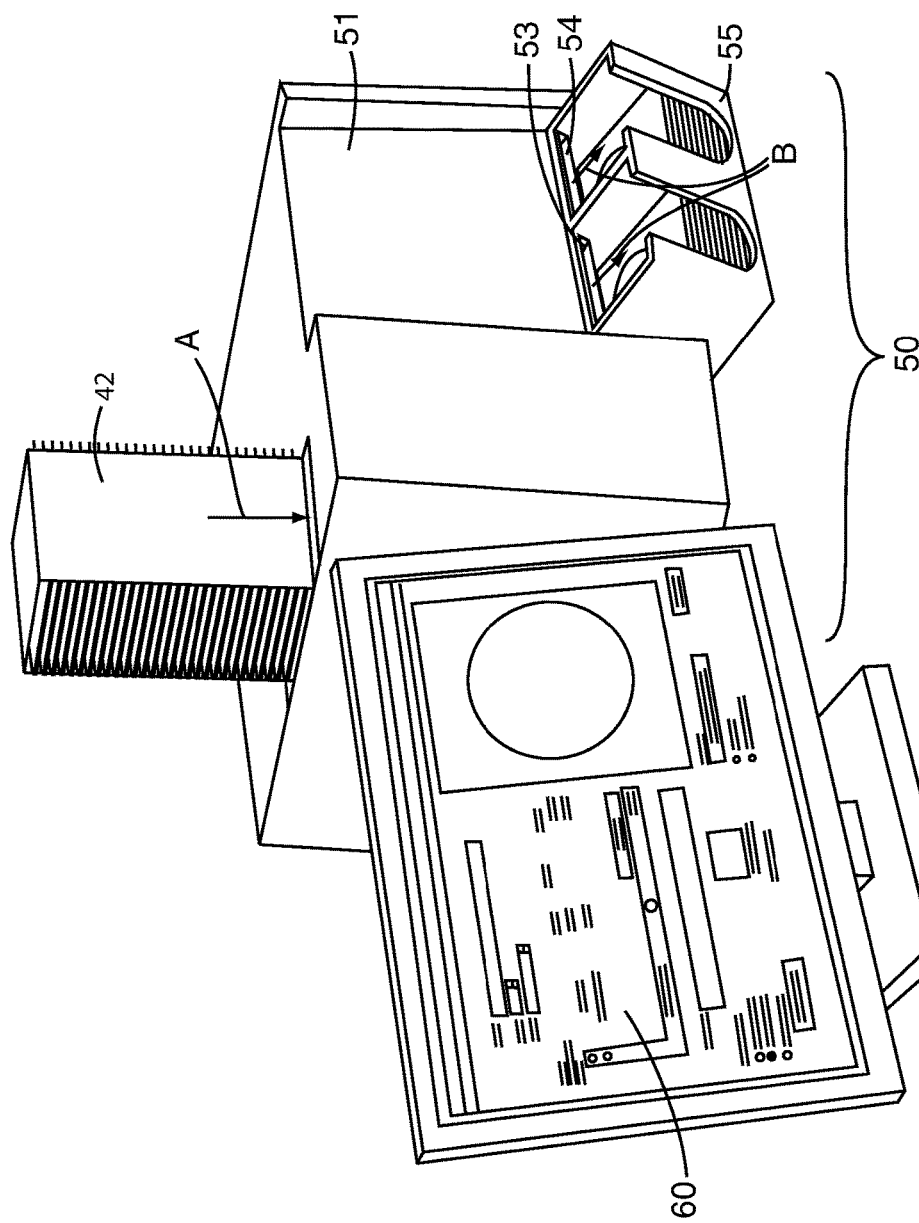
FIG. 11 is a perspective view of the reader module and monitor of the modular apparatus and system of FIG. 4.

FIG. 11. shows a perspective view of one embodiment of a reader module 50 with one embodiment of an optional display 60 (e.g., monitor). The reader module 50 comprises a detector (not shown) housing 51, slots 53 and 54, and collator 55. Also shown in FIG. 11 is a stacking tray 42, which is being fed into the housing 51 in the direction indicated by arrow A, and culture devices 70, which are being ejected from the housing 51 into collator 55 in the direction indicated by arrows B.

In a preferred embodiment, reader module 50 houses an imaging device (detector), such as a 2-dimensional monochromatic camera for generating one or more images of an inserted culture device 70. In addition, reader module 50 may house various illuminators for illuminating the front and back of culture device 70 during imaging. The illuminators can illuminate culture device 70 with one or more colors, and one or more images of culture device 70 can be generated and then analyzed to determine bacteria counts on culture device 70 as described in, e.g., U.S. Pat. No. 7,298,885 and U.S. Patent Application Publication No. 2005/0053265 (Graessle et al). In some embodiments, reader module 50 may process images of different culture devices 70 according to different image processing profiles as described in U.S. Pat. No. 7,298,885 and U.S. Patent Application Publication No. 2005/0053265 (Graessle et al). The detector provides analysis data that can be used by another part of the modular system, such as a data processor which can comprise an executable algorithm, for example.

By way of example, culture devices 70 may comprise a culture device sold by 3M under the trade name PETRIFILM plates. Culture device 70 can be utilized to facilitate the rapid growth and detection of bacteria or other biological agents commonly associated with food contamination, including, for example, aerobic bacteria, *E. coli*, coliform, *Enterobacteriaceae*, yeast, mold, *Staphylococcus aureus*, *Listeria*, *Campylobacter*, or the like.

Reader module 50 may also include accessory features, such as a display 60 to display the progress or results of analysis of the culture device 70 to a user. Other features may include, for example, a hinged door to facilitate access to each module.

In some embodiments, reader module 50 includes an internal processor for analyzing the detection results of culture devices 70. In other embodiments, however, the processing of images occurs external to reader module 50, e.g., in a desktop computer, workstation, or the like. In the latter case, reader module 50 may include an interface to allow the reader module 50 to be communicatively coupled to another computer.

Referring again to FIG. 11, the reader module 50 ejects culture devices 70 into collator 55 when the detection step associated with reader module 50 is complete. Collator 55 organizes culture devices 70 after the detection step is performed in the one or more modules, such as reader module 50, provided for that function. Culture devices 70 can be sorted in the collator 55 according to an analysis performed by the internal or external processor. A user can establish at least one criterion used by the processor such that the culture devices 70 can be collated into at least one or more stacks. Examples of sort criteria could be origin of sample, medium plate type, CFU enumeration ranges, date of test, number of media, a test result condition (e.g. pass, fail, test error, uninterpretable result, or retest), etc.

Figure 12:
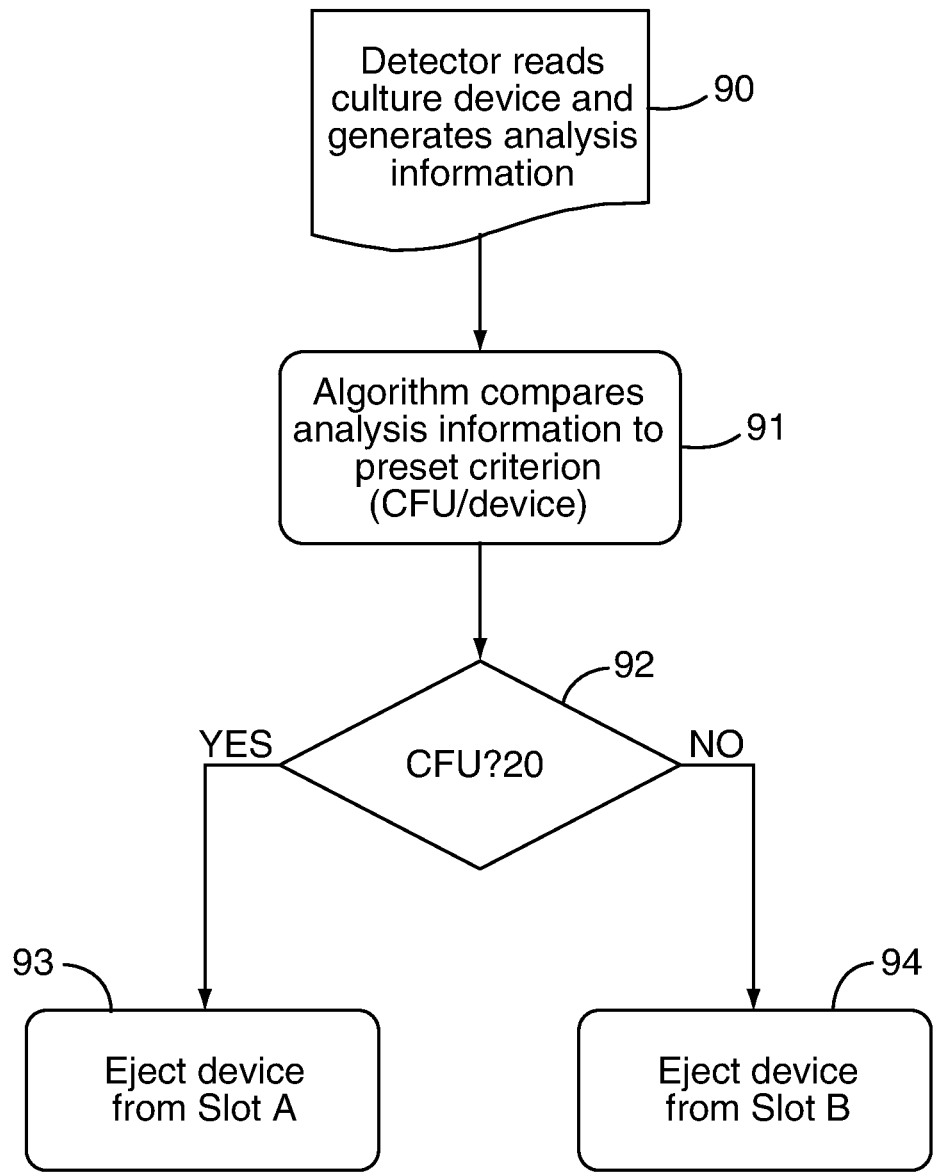
FIG. 12 is a block diagram of an exemplary process to determine whether a condition exists in a culture device.

The processor can be used (e.g., with an algorithm) to determine whether a condition is present in culture medium 70. The condition may be determined by at least one criterion such as, for example, a sample identifier, a test identifier (e.g. type of test, number of test samples, type of media in the culture device 70, etc.), or a test result. FIG. 12 illustrates a block diagram of an exemplary embodiment showing how a processor can use analysis information to determine whether one, or perhaps more than one, condition exists in a culture device. In this example, the processor can be programmed with a preset criterion (e.g., less than or equal to 20 colony-forming units (CFU) in the culture device) which establishes a condition for a test result. In step 90, the culture device is scanned by the detector and the detector provides the analysis information (e.g., CFU/culture device) for the processor. In the step 91, the processor compares the analysis information to the preset criterion and a decision 92 is made. If the culture device contains less than or equal to 20 CFU, then the condition exists and the culture device is ejected from Slot A of the reader module 93. If the culture device contains more than 20 CFU, then the condition does not exist and the culture device is ejected from Slot B of the reader module 94.

It is anticipated that more than one criterion may be used to determine whether a condition exists. For example, one criterion may be based on the presence of a certain type of organism, such as *Escherichia coli*, in a mixed culture in the culture device and the second criterion may be based on the number of *E. coli* colonies present. Two other criteria that may be used in combination to define a condition may include the presence of a certain organism and a particular sample type (e.g., dairy, meat, etc.). It is also anticipated that three criteria, four criteria or five criteria may be used to determine whether a condition exists. It is also anticipated that more than one criterion may be used to determine whether more than one condition exists, e.g., at least a second condition, at least a third condition, at least a fourth condition or at least a fifth condition may exist.

Other System Components

Modular sample processing and/or detection systems can comprise an external computer which performs control of the process steps in one or more modules, and/or analysis of the detection data generated by the reader module, as described herein. The external computer may include, for example, a microprocessor programmed for image analysis of culture devices. The external computer may comprise a personal computer (PC), desktop computer, laptop computer, handheld computer, workstation, or the like, and can perform functions such as maintaining system configuration, performance logs, and higher systems communications.

The modular systems can be coupled to the external computer via an interface, such as a Universal Serial Bus (USB) interface, a Universal Serial Bus 2 (USB2) interface, an IEEE 1394 FireWire interface, a Small Computer System Interface (SCSI) interface, an Advance Technology Attachment (ATA) interface, a serial ATA interface, a Peripheral Component Interconnect (PCI) interface, a conventional serial or parallel interface, or the like. In a preferred embodiment, the modular system communicates and self identifies on a real time local communication bus to arbitrate time critical events, such as positioning of the culture device within a module and/or intermodule transport of the culture device, and a command and data bus operating from a host computer.

The external computer can perform control of the process steps in one or more modules, and/or analysis of the detection data generated by the reader module. Software for performance functions can be loaded on external computer, such as user software, system control software, sample under test indicia software (e.g., to recognize or otherwise indicate the source of a sample) which may be optionally read by sample under an indicia reader. Depending on the culture device and detection processes, the external computer may also include database software and enumeration software.

Modular sample processing and/or detection systems can be linked to an internet or intranet via a server or a remote server. This type of linkage can be used for remote servicing, reduced service cost, and monitoring customer usage trends (for example, plate types, usage patterns, and detecting unintended behavior, etc.) with customer usage software. Remote diagnostics could be used to further control service costs as performance of the system could be monitored remotely to predict component failures and periodic maintenance such as cleaning. Operational changes including software updates could also be made remotely (for example, reflash firmware).

Modular sample processing and/or detection systems can be based on a limited distributed intelligence model. Enough control of system can reside locally to the respective modules to enable local functions. Hierarchical control can be from an external computer and/or a network server running a hosting application and graphical user interface. These applications can link by various known operating systems (e.g., dll, windows, etc.).

Methods

Modules, modular systems and apparatus of the present disclosure can be used in methods to detect a microorganism in a sample. The methods can include steps to prepare a sample for detecting a microorganism, steps to detect the microorganism, and steps to determine whether a condition exists in a culture device. A condition that exists in a culture device may be indicative of a condition that exists in the sample (i.e., microbial contamination).

In one embodiment, the method includes providing a culture device, a liquid sample, a data processor which uses analysis information to determine whether one or more conditions exist, and at least two modules. At least one module can include a detector for analyzing the culture device and providing analysis information. The module comprising a detector can further include a housing in which slots are formed. A first slot can be formed for receiving the culture device, a second slot can be formed for ejecting the culture device from the housing if one ore more conditions exist, and a third slot can be formed for ejecting the culture device from the housing if the one or more conditions do not exist. The method can further comprise feeding the culture device into at least one of the modules, using the detector to analyze the culture device to provide analysis information for the data processor, and determining whether one ore more conditions exist in the culture device. The method may further comprise providing a sample reservoir module and holding a sample reservoir thereon, providing a liquid processing module and transferring a liquid sample therein, or providing a stacking tray loader module and transferring culture devices to a stacking tray therein.

A number of embodiments of a module have been described. Nevertheless, various modifications may be made without departing from the spirit and scope of the invention. For example, one or more features described herein may be used with or without other described features. For example, one or more of modules may be eliminated. These and other embodiments are within the scope of the following claims.

All references and publications cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

EMBODIMENTS

1. A modular system for detecting microorganisms, the system comprising
at least two modules, wherein each module performs at least one step in the process of detecting the microorganism, and
a culture device,
wherein the modules are aligned to allow for transfer of the culture device from one module to another.
2. A modular system for detecting microorganisms, the system comprising
at least two modules, wherein each module performs at least one step in the process of detecting the microorganism, and
a culture device,
and interlocking features to align the modules for transfer of the culture device from one module to another.
3. A modular system for detecting microorganisms, the system comprising
at least two modules, wherein each module performs at least one step in the process of detecting the microorganism, and
a plurality of culture devices,
wherein at least one module comprises a means for detecting the microorganism on the culture device and at least one module comprises a means for collecting the plurality of culture devices.
4. The system of embodiment 2, wherein the interlocking features align the modules in a predetermined sequential order.
5. The system of embodiment 2, wherein the interlocking features are mechanical.
6. The system of embodiment 2, wherein the interlocking features are electrical.
7. The system of embodiment 2, wherein the interlocking features are optical.
8. The system of any of embodiments 1-3, the system further comprising a host computer.
9. The system any of embodiments 1-2, further comprising a processor that quantifies biological agents detected in the culture device.
10. The system of any of embodiments 1-2, wherein at least one of the modules is a reader that reads the biological agents in the culture device with an imaging device.
11. The system of embodiment 10, wherein the imaging device comprises a camera.
12. A modular system for detecting a microorganism in a sample, the system comprising:
first and second modules, wherein each module performs at least one step in the process of preparing the sample to detect the microorganism;
at least one sample reservoir unit; and
a culture device;
wherein the first module is configured to hold at least two sample reservoir units, each unit comprising a liquid sample;
wherein the second module is configured to transfer the liquid sample from the at least one sample reservoir unit to the culture device; and
wherein the modules are aligned to allow for transfer of the liquid sample from the first module to the second module.
13. A modular system for detecting a microorganism in a sample, the system comprising:
a culture device;
a data processor which uses analysis information to determine whether one or more conditions exist in the culture device; and
a module to provide the analysis information, wherein the module comprises
a housing
a first slot formed in a first side of the housing for receiving the culture device;
a second slot formed in the housing for ejecting the culture device from the housing when the one or more conditions are present in the culture device;
a third slot formed in the housing for ejecting the culture device from the housing when the one or more conditions are not present in the culture device; and
a detector for analyzing the culture device.
14. A modular system for processing and/or detecting a microorganism, the system comprising:
a culture device;
a first module configured to hold a sample reservoir unit comprising a liquid sample;
a second module configured to transfer the liquid sample to the culture device;
a third module comprising a housing and a detector, wherein a first slot is formed in the housing for receiving the culture device and a second slot is formed in the housing for ejecting the culture device from the housing; and
interlocking features to align two or more of the foregoing modules.
15. The system of embodiment 14 further comprising a data processor which uses at least one preset criterion to determine whether one or more conditions exist in the culture device.
16. The system of embodiment 15 wherein the third module further comprises a third slot formed in the housing for ejecting the culture device from the housing.
17. The system of embodiment 15 wherein the culture device is ejected from the second slot of the housing when the one or more conditions exist.
18. The system of embodiment 15 wherein the culture device is ejected from the third slot of the housing when the one or more conditions do not exist.
19. The system of any one of embodiments 12-18, further comprising a host computer.
20. The system of any one of embodiments 12-19, further comprising interlocking features to align at least two modules.
21. The system of embodiment 20, wherein the interlocking features are reversibly interlocking.
22. The system of embodiment 20, wherein the interlocking features align the modules in a predetermined sequential order.
23. The system of embodiment 20, wherein the interlocking features are mechanical.

24. The system of embodiment 20, wherein the interlocking features are electrical.
25. The system of embodiment 20, wherein the interlocking features are optical.
26. The system of embodiment 12 or 14, wherein the sample reservoir units further comprise an indicium.
27. The system of any one of embodiments 12-26, wherein the first module further comprises an indicium reader.
28. The system of embodiment 12 or 14, wherein the second module comprises a sample distributor.
29. The system of embodiment 28, wherein the sample distributor further comprises at least one liquid reservoir.
30. The system of embodiment 12 or 14, wherein the second module further comprises a component selected from the group consisting of a culture device opener, an indicium reader, a culture device storage unit, a culture device labeler, a culture device conveyor, and a combination of any two or more of the foregoing.
31. The system of embodiment 28, wherein the culture device opener comprises a vacuum source.
32. The system of embodiment 12 or embodiment 14, further comprising a disposal station.
33. The system of embodiment 13 or embodiment 17, wherein the second slot or third slot is located on a second side of the housing.
34. The system of embodiment 13 or embodiment 17, wherein the second slot and third slot are located on a second side of the housing.
35. A module for processing and/or detecting a microorganism, the module comprising:
a housing,
a first slot formed in a first side of the housing for receiving a culture device;
a second slot formed in a second side of the housing for ejecting the culture device following the performance of a processing step in the module; and
interlocking features to align the module with another module.
36. A method for detecting a microorganism, the method comprising
providing at least two modules of embodiment 35,
feeding a culture device into at least one of the modules, and
detecting the microorganism in the culture device in at least one of the modules.
37. A method for detecting a microorganism, the method comprising
providing a culture device, a liquid sample, a data processor which uses analysis information to determine whether one or more conditions exist, and at least two modules;
wherein a first module comprises,
a detector for analyzing the culture device and providing analysis information for the data processor; and
a housing comprising a first slot formed in the housing for receiving the culture device, a second slot formed in the housing for ejecting the culture device from the housing if one or more conditions exist, and a third slot formed in the housing for ejecting the culture device from the housing if the one or more conditions do not exist;
feeding the culture device into at least one of the modules;
using a detector to analyze the culture device to provide analysis information for the data processor; and
using the data processor to determine whether one or more conditions exist in the culture device.

38. The method of embodiment 37, further comprising providing a sample reservoir module and holding a sample reservoir thereon.
39. The method of embodiment 37 or 38, further comprising providing a liquid processing module and transferring a liquid sample therein.
40. The method of any of embodiments 37-39, further comprising providing a stacking tray loading module and the step of transferring a culture device therein.

A number of embodiments of a module have been described. Nevertheless, various modifications may be made without departing from the spirit and scope of the invention. For example, one or more features described herein may be used with or without other described features. For example, one or more of modules may be eliminated. These and other embodiments are within the scope of the following claims.

All references and publications cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

What is claimed is:
1. A method for detecting a microorganism, the method comprising
(i) inserting a culture device into a modular system, the modular system comprising a plurality of freestanding modules, the plurality of freestanding modules including:
a freestanding first module configured to hold a stomacher bag comprising a liquid sample;
a freestanding second module configured to transfer the liquid sample to the culture device; and
a freestanding third module comprising a housing and a detector, wherein a first slot, a second slot, and a third slot are formed in the housing of the freestanding third module, the freestanding third module configured to receive the culture device through the first slot;
interlocking features to align two or more freestanding modules of the plurality of freestanding modules; and
a data processor, wherein the data processor is programmed to:
receive at least one user-established preset criterion that defines a quantity of microorganism colonies;
receive colony count information from the detector;
compare the colony count information to the at least one preset criterion to determine whether one or more conditions exist in the culture device;
configure the freestanding third module to eject the culture device through the second slot when the one or more conditions exist in the culture device; and
configure the freestanding third module to eject the culture device through the third slot when the one or more conditions do not exist in the culture device;
(ii) analyzing the culture device for colony count information with the detector; and
(iii) provide the colony count information from the detector to the data processor.

2. The method of claim 1, wherein the modular system comprises a sample reservoir module and holding a sample reservoir thereon.

3. The method of claim 1, wherein the modular system comprises a liquid processing module and the method further comprises the step of transferring a liquid sample to the liquid processing module.

4. The method of claim 1, wherein the at least one preset criterion includes a second preset criterion that includes the microorganism type.

5. The method of claim 1, wherein the at least one preset criterion includes a second preset criterion that includes the plate type.

6. The method of claim 1, wherein the at least one preset criterion includes a second preset criterion that includes the sample type.

7. The method of claim 1, wherein the modular system further comprises a collator, and further comprising the step of that operating the collector cooperatively with the processor to collate the culture devices according to the at least one preset criterion.

8. The method of claim 1, wherein:

each respective freestanding module of the plurality of freestanding modules comprising a respective housing, and for each respective freestanding module of the plurality of freestanding modules, the housing of the respective freestanding module defines one or more of the interlocking features, the interlocking features of the respective freestanding module aligning the respective freestanding module with one or more freestanding modules of the plurality of freestanding modules, each of the one or more interlocking features of the respective freestanding module being at least one of a projection or an indentation, wherein the interlocking features defined by the housings of the freestanding modules of the plurality of freestanding blocks are shaped such that the plurality of freestanding modules are capable of being aligned in a predetermined sequential order for use but prevent configuration of the plurality of freestanding modules in an order that prevents or inhibits sample processing or detection.

* * * * *